(12) United States Patent
Godwin et al.

(10) Patent No.: US 10,643,003 B2
(45) Date of Patent: May 5, 2020

(54) SYSTEM AND METHOD FOR MAINTAINING PRIVACY OF DATA USED AT A SIGNATURE CAPTURE DEVICE

(71) Applicant: Ateb, Inc., Raleigh, NC (US)

(72) Inventors: Sharen Ann Godwin, Wilmington, NC (US); Frank Phillip Sheppard, Raleigh, NC (US)

(73) Assignee: Ateb, Inc., Raleigh, NC (US)

( * ) Notice: Subject to any disclaimer, the term of this patent is extended or adjusted under 35 U.S.C. 154(b) by 0 days.

(21) Appl. No.: 16/215,034

(22) Filed: Dec. 10, 2018

(65) Prior Publication Data

US 2019/0340386 A1    Nov. 7, 2019

Related U.S. Application Data

(63) Continuation-in-part of application No. 13/102,570, filed on May 6, 2011, now abandoned, which is a continuation-in-part of application No. 12/494,651, filed on Jun. 30, 2009, now Pat. No. 8,139,731, which is a continuation of application No. 10/672,556, filed on Sep. 25, 2003, now Pat. No. 7,558,380, which is a continuation-in-part of application No. 13/102,570, filed on May 6, 2011, now abandoned, which is a continuation-in-part of application No. 11/375,516, filed on Mar. 14, 2006, now abandoned.

(51) Int. Cl.
*G06F 21/62* (2013.01)
*G16H 20/10* (2018.01)
*G06Q 30/06* (2012.01)

(52) U.S. Cl.
CPC ...... *G06F 21/6254* (2013.01); *G06F 21/6245* (2013.01); *G06Q 30/0635* (2013.01); *G16H 20/10* (2018.01)

(58) Field of Classification Search
CPC .................. G06F 21/6245; G06F 21/6254
See application file for complete search history.

(56) References Cited

U.S. PATENT DOCUMENTS

| | | | |
|---|---|---|---|
| 6,236,975 B1 * | 5/2001 | Boe ............ | G06Q 30/02 705/14.19 |
| 6,240,394 B1 * | 5/2001 | Uecker ............ | G06Q 10/10 705/3 |

(Continued)

OTHER PUBLICATIONS

Song, Won Jay; Ahn, Byung Ha; "Secure Transmission of the Prescription Order Communication System Based on the Internet and the Public-Key Infrastructure Using Master Smart Cards in the 2-Way Type Terminal", Proceedings of the 35th Annual Hawaii International Conference on System Sciences, IEEE, Jan. 10, 2002, 8 pgs.*

(Continued)

*Primary Examiner* — Victor Lesniewski
(74) *Attorney, Agent, or Firm* — Kilpatrick Townsend & Stockton LLP

(57) ABSTRACT

A signature capture device is used to display a targeted message for a customer picking up an ordered item. The targeted message is selected based on an identifier for the ordered item. Personal information used for the display message is managed to maintain security and privacy of the information. In one embodiment, the ordered item is a prescription and the signature capture device is part of a pharmacy management system.

18 Claims, 22 Drawing Sheets

(56) References Cited

U.S. PATENT DOCUMENTS

| | | | | |
|---|---|---|---|---|
| 6,732,113 | B1* | 5/2004 | Ober | G06F 19/324 |
| 6,910,208 | B1* | 6/2005 | Zimniewicz | G06F 9/453 |
| | | | | 717/174 |
| 8,473,452 | B1* | 6/2013 | Ober | G06F 19/326 |
| | | | | 707/607 |
| 2001/0047281 | A1* | 11/2001 | Keresman, III | G06F 21/6245 |
| | | | | 705/2 |
| 2002/0007285 | A1* | 1/2002 | Rappaport | G06F 19/325 |
| | | | | 705/2 |
| 2002/0032582 | A1* | 3/2002 | Feeney, Jr. | G06F 19/3462 |
| | | | | 705/2 |
| 2002/0099273 | A1* | 7/2002 | Bocionek | A61B 5/411 |
| | | | | 600/300 |
| 2003/0061096 | A1* | 3/2003 | Gallivan | G06Q 50/22 |
| | | | | 705/14.66 |
| 2003/0105667 | A1* | 6/2003 | Millikan | G06Q 30/02 |
| | | | | 705/14.58 |
| 2004/0019502 | A1* | 1/2004 | Leaman | G06F 19/326 |
| | | | | 705/2 |
| 2004/0019794 | A1* | 1/2004 | Moradi | G06Q 50/22 |
| | | | | 713/185 |
| 2004/0078237 | A1* | 4/2004 | Kaafarani | G06F 19/3456 |
| | | | | 705/2 |
| 2004/0117205 | A1* | 6/2004 | Reardan | G06F 19/328 |
| | | | | 705/2 |
| 2004/0148195 | A1* | 7/2004 | Kalies | G06F 19/326 |
| | | | | 705/2 |
| 2004/0172295 | A1* | 9/2004 | Dahlin | G06F 19/3456 |
| | | | | 705/2 |
| 2004/0215981 | A1* | 10/2004 | Ricciardi | G06Q 10/10 |
| | | | | 726/27 |
| 2004/0256453 | A1* | 12/2004 | Lammle | G06F 19/3456 |
| | | | | 235/381 |
| 2005/0004700 | A1* | 1/2005 | DiMaggio | G06F 19/3462 |
| | | | | 700/213 |
| 2005/0010448 | A1* | 1/2005 | Mattera | G06Q 10/10 |
| | | | | 705/3 |
| 2005/0021173 | A1* | 1/2005 | Pinney | G06F 19/3462 |
| | | | | 700/231 |
| 2005/0069103 | A1* | 3/2005 | DiVenuta | G06Q 40/08 |
| | | | | 379/88.18 |
| 2005/0165623 | A1* | 7/2005 | Landi | G06F 21/6254 |
| | | | | 705/2 |
| 2005/0182662 | A1* | 8/2005 | Pierce | G06Q 10/10 |
| | | | | 705/3 |
| 2006/0178913 | A1* | 8/2006 | Lara | G16H 40/20 |
| | | | | 705/3 |
| 2006/0235726 | A1* | 10/2006 | Paraison | G06F 19/3456 |
| | | | | 705/2 |
| 2006/0247968 | A1* | 11/2006 | Kadry | G06Q 30/02 |
| | | | | 705/14.53 |
| 2006/0266826 | A1* | 11/2006 | Banfield | G06Q 10/10 |
| | | | | 235/383 |
| 2007/0027712 | A1* | 2/2007 | Lapsker | G09F 5/04 |
| | | | | 705/2 |
| 2007/0124172 | A1* | 5/2007 | Moura | G06Q 10/087 |
| | | | | 705/2 |
| 2007/0174079 | A1* | 7/2007 | Kraus | G06Q 10/10 |
| | | | | 705/3 |
| 2008/0147554 | A1* | 6/2008 | Stevens | G06F 21/6254 |
| | | | | 705/51 |
| 2010/0169218 | A1* | 7/2010 | Wang | G06F 19/3456 |
| | | | | 705/50 |
| 2011/0301968 | A1* | 12/2011 | Godwin | G06F 19/00 |
| | | | | 705/2 |
| 2016/0292456 | A1* | 10/2016 | Dubey | G06F 21/6245 |

OTHER PUBLICATIONS

Moore, Jerry; Hobson, Greg; Waldman, Gary; Wootton, John; "A real-time visual inspection system for automated prescription dispensing", International Conference on Systems, Man and Cybernetics, IEEE, Oct. 8-11, 2000, pp. 577-582.*

* cited by examiner

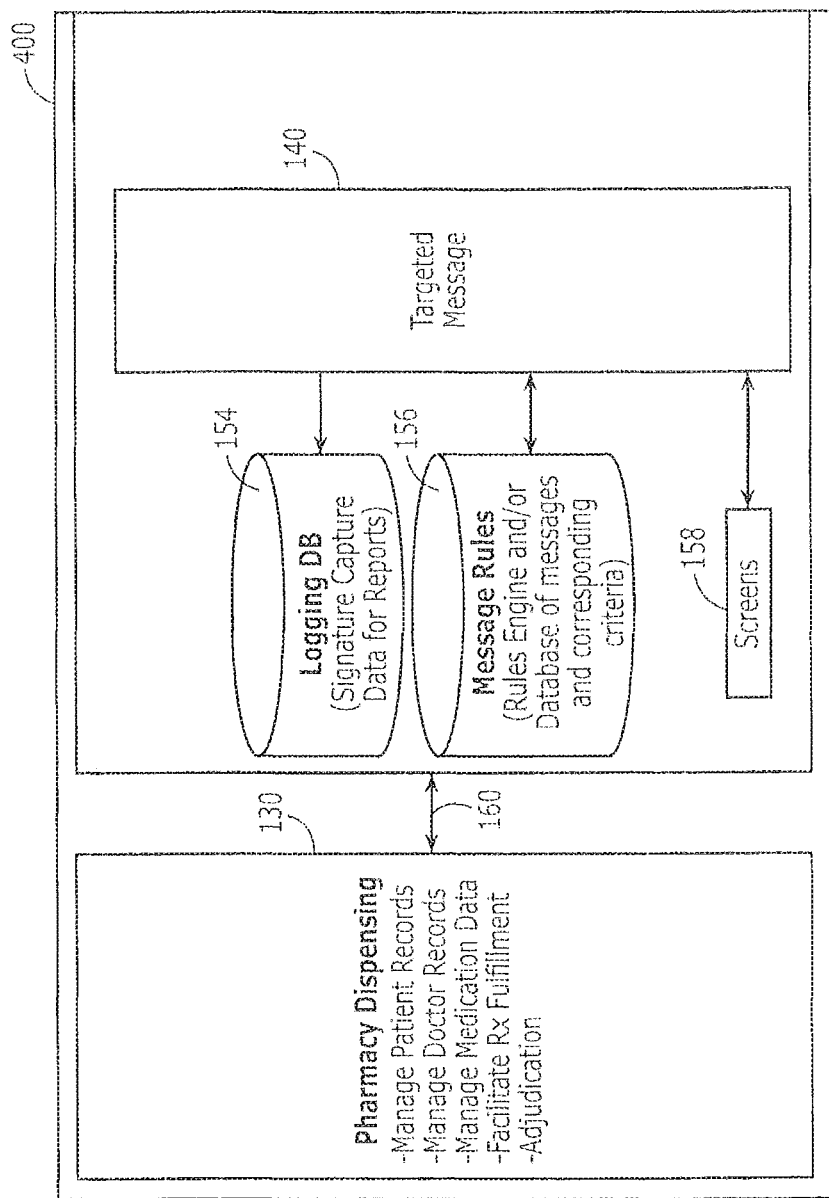

| Field Name |
|---|
| Rx Number |
| Store Number |
| *Rx Information Section* |
| Refills Remaining |
| Expiration Date |
| Last Fill Date |
| Date of First Fill |
| Days Supply on Last Fill |
| Original Refills Authorized |
| Last Fill Quantity |
| Quantity Remaining |
| Original Fill Quantity |
| Last Fill Price |
| Reassigned Rx Number |
| Status |
| Refills in Queue |

FIG. 13A

| |
|---|
| SIG Text |
| *Patient Information* |
| Social Security Number |
| Personal Identification No. |
| Name |
| Birth Date |
| Telephone No. - Primary |
| Telephone No. - Secondary |
| Street Address |
| City |
| State Province |
| Zip Postal Code |
| Driver's License Number |
| Store Charge Account |
| Our Dial Permission |
| *Drug Information* |
| Drug Name |
| Drug NDC |
| Schedule of Drug |
| Manufacturer Name |
| Quantity on Hand |
| Therapeutic Class |
| *Doctor Information* |
| Name |
| Telephone Number |
| Fax Number |
| Street Address |
| City |
| State Province |
| Zip Postal Code |

FIG. 13B

| Field Name |
| --- |
| Rx Number |
| Store = |
| Social Security Number |
| Personal Identification Number |
| Order Quantity |
| Pickup Data |
| Pickup Time |
| Delivery Method |
| Drug Name |
| Call Back Phone Number |
| Connect |
| Payment Method |
| Authorize Additional Refills |
| Generic Substitution Allowed |

FIG. 13C

| Rx # | Patient | Medication | New Refill | Ack | Safety Caps | Counseling |
|---|---|---|---|---|---|---|
| 6671231 | JOHN SMITH | AMOXICILLIN | N | N | Yes | Accept |

| Remove All Rx | Page Up | Page Down | Manual Add | Main Menu | Next → |

FIG. 14A

| Rx # | Patient | Medication | New Refill | Ack | Safety Caps | Counsel |
|---|---|---|---|---|---|---|
| 6671231 | JOHN SMITH | AMOXICILLIN | N | N | Yes | Accept |

← Back | Accept | Decline | Privacy Statement

FIG. 14B

| Rx # | Patient | Medication | New Refill | Ack | Safety Caps | Counsel |
|------|---------|------------|------------|-----|-------------|---------|
| 6671231 | JOHN SMITH | AMOXICILLIN | N | N | Yes | Accept |

Introduction
"Ateb is committed to your right to privacy and to keeping your personal information private. Because we understand the importance of maintaining your privacy we developed Ateb's Privacy Policy to inform you of our policies and practices regarding information we obtain from you on this site. It takes approximately 2 minutes to hear the entire Ateb privacy policy. Press "9" at any time to exit the Privacy Policy and continue processing your refill.

Privacy Policy
Use and Disclosure of Information
Except as otherwise stated, we may use information collected via this survey to communicate information to you (if you have requested it), for our marketing and research purposes, and for any other purpose specified. In addition, we may make full use of all information acquired through this survey that is not in personally identifiable form.

If you provide personally identifiable information in this survey, we may combine such information with other actively collected information unless we specify otherwise at the point of collection. We may disclose personally identifiable information you provide via this survey to affiliates of Ateb Inc. or Ateb, worldwide that agree to treat in accordance with this Privacy Policy and use it for the same purposes. We also may disclose personally identifiable information you provide via this survey to third parties that are not affiliates of Ateb Inc., but only:
- To contractors we use to support our business (such as fulfillment services, technical support, delivery services, and financial institutions) in which case we will require such third parties to agree to treat it in accordance with this Privacy Policy and use it for the same purposes;
- in connection with the sale, assignment, or other transfer of the business of this site to which the information relates, in which case we will

[← Back]  [Accept]  [Decline]  [Privacy Statement]

FIG. 14C

| Rx # | Patient | Medication | New Refill | Ack | Safety Caps | Counsel |
|---|---|---|---|---|---|---|
| 6671231 | JOHN SMITH | AMOXICILLIN | N | N | Yes | Accept |

RX # 987654

Please sign in the box

[← Back] [Cancel] [Page Up] [Page Down] [Clear Sig] [Submit Sig]

FIG. 14D

SYSTEM AND METHOD FOR MAINTAINING PRIVACY OF DATA USED AT A SIGNATURE CAPTURE DEVICE

CROSS-REFERENCES TO RELATED APPLICATIONS

This application is a Continuation-in-Part of U.S. patent application Ser. No. 13/102,570, filed May 6, 2011. U.S. patent application Ser. No. 13/102,570 is a Continuation-in-Part of U.S. patent application Ser. No. 12/494,651, filed Jun. 30, 2009, which is a continuation of U.S. patent application Ser. No. 10/672,556, filed Sep. 25, 2003. U.S. patent application Ser. No. 13/102,570 is also a Continuation-in-Part of U.S. patent application Ser. No. 11/375,516, filed Mar. 14, 2006. The disclosures of all of the aforementioned U.S. patent application Ser. Nos. 13/102,570, 12/494,651, 10/672,556 and 11/375,516 are incorporated by reference herein in their entireties.

BACKGROUND OF THE INVENTION

Signature capture devices are used to handle various aspects of delivery or receipt of items and services. For example, a signature capture/display device maybe located at a retail or public counter where a customer requests and receives an ordered item. The signature capture system may include a signature capture touch screen for receiving a signature using a stylus or special pen. The touch screen may also provide a series of touch screen buttons, display a series of screens, and accept a series of user inputs, e.g., to acknowledge receipt of an item or information concerning the item.

Embodiments of the invention provide further functionality to a management system that processes ordered items using a signature capture device, by identifying a targeted message for display on the signature capture device. Such targeted messages introduce technical issues relating to the privacy of the message, such as the information that is displayed in the message or that is received from a customer in response to the message. Privacy may be a significant issue not only for the customer (e.g., access to personal information by others), but also an issue for the system managing the ordered item, where information used and collected in response to a targeted message adds responsibility and system complexity in securing any personal or private information. As an example, where the ordered item is a prescription being picked up at a pharmacy, if a customer leaves the counter without responding to a displayed message, the message (and any information relating to the customer prescription) may still be displayed and seen when the next customer approaches the counter. As a further example, if a customer provides a response to a targeted message, the nature of that response may reveal information about the customer or about the item received. In the case of a prescription, the response may reveal information about a particular disease or condition of the customer that is being treated, and may be subject to privacy/security requirements for receiving and storing such information within the pharmacy system. While receiving and using personal information is often an inherent part of interaction with customers in many environments, such as in pharmacy systems and operations, each incremental increase in the receipt or use of personal information correspondingly increases system cost, risk and complexity in preserving information security and privacy. Embodiments of the invention address issues relating to the privacy of customer information, by reducing or managing the amount of personal information that is used at a signature capture device, or that is stored in an associated system as a result of using a signature capture device.

SUMMARY OF THE INVENTION

Embodiments of the invention relate to the use and collection of information at a signature capture system/device where targeted messages may be displayed, such as personal information of customers/recipients picking up an ordered item.

In some described embodiments, a signature capture device is used with a pharmacy management system to capture the signature of a customer and to display targeted messages for the customer. Targeted messages are identified using a pharmacy dispensing database and a messaging rules database. Information relating to the targeted message (such as responses from the customer) are stored in a logging database. Personal information displayed, collected or used at the signature device is processed at the pharmacy management system to maintain the security and privacy of such information.

In some embodiments, and in order to identify a targeted message, an identifier for a pharmaceutical prescription (ordered item) is received at the pharmacy management system and is used to query the pharmacy dispensing database in order to retrieve predefined criteria relating to a specific pharmaceutical prescription, with personal identifying data for the customer removed from the predefined criteria. The predefined criteria is used to query the messaging rules database, to identify a targeted message for the customer. The targeted message is displayed at the signature capture device, but is removed after a predetermined period of time to minimize the opportunity for others to see the targeted message. When a response to the targeted message is received from the customer at the signature capture device, the response is stored in the logging database, but with the response de-identified, to minimize the amount of personal information being collected and system complexity and cost associated with securing such information.

In one embodiment, a method manages the security of personal information at a management system that processes ordered items using a signature capture device. The method includes receiving identification of an ordered item (e.g., a pharmaceutical prescription) at the management system; accepting, at the signature capture device in the management system, a signature from a person receiving the ordered item; querying a first database (e.g., a pharmacy dispensing database) in the management system, using the identification of the ordered item, to retrieve predefined criteria based on the identification of the ordered item, wherein the retrieved predefined criteria does not include personal identifying data for the person receiving the ordered item; querying a second database (e.g., a messaging rules database) in the management system using the predefined criteria to identify a targeted message; displaying the targeted message on the signature capture device for viewing by the person receiving the ordered item, wherein the targeted message is removed from the signature capture system after a predetermined period of time; receiving, at the signature capture system, a response to the targeted message from the person receiving the ordered item, and providing the received response to a third database (e.g., a logging database) in the management system, including de-identifying the received response to maintain the privacy of personal information of the person receiving the ordered item.

While some described embodiments relate to a management system using a signature capture device in a pharmacy environment, other embodiments of the present invention may be employed in a non-pharmacy environment, wherein targeted messages may be provided and personal information used at a signature capture system based on an identification other than a pharmaceutical prescription, such as an employee number, a Social Security number, a credit card number, a zip code and/or an insurance identification number, using predefined criteria based on the user input to identify a targeted message. For example, in a retail environment, wherein a scanner is used to scan barcodes on goods, a signature capture device may be used to obtain a credit card/debit card authorization for the purchase of goods. A targeted message may be provided on the signature capture device based on attributes of the purchaser from the purchaser's credit card/debit card account information. Any personal information displayed, collected and used at the signature capture system is managed for security and privacy.

BRIEF DESCRIPTION OF THE DRAWINGS

FIGS. 4A and 4B are block diagrams of systems, methods and/or computer program products for providing targeted messages in a pharmacy according to other embodiments of the present invention.

FIGS. 13A-13C illustrate attributes that may be used to identify a targeted message according to some embodiments of the present invention.

FIGS. 14A-14D are screen shots of targeted message screens that may be displayed on a signature capture system according to some embodiments of the present invention.

DETAILED DESCRIPTION

Figure 1:
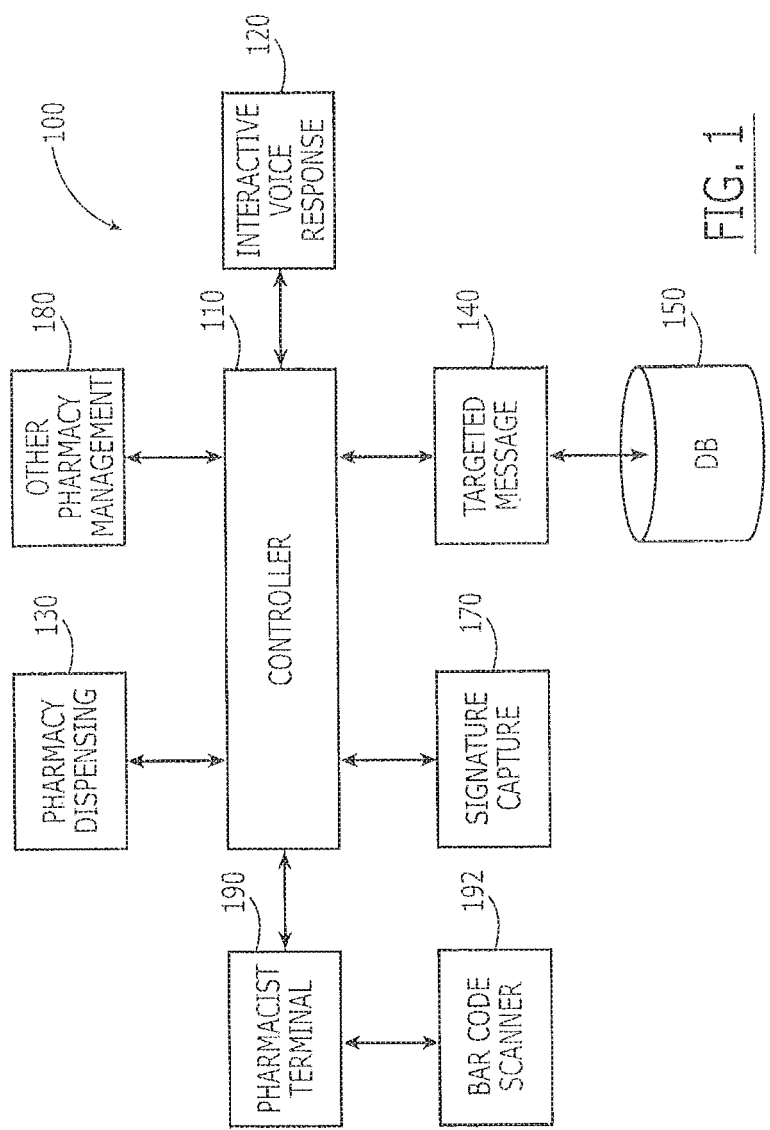
FIG. 1 is a block diagram of systems, methods and/or computer program products for providing targeted messages in a pharmacy according to some embodiments of the present invention.

Described embodiments of the invention relate to the use and management of data at a signature capture system/device in a pharmacy management system. As explained earlier, in the dispensing of prescription items at a pharmacy counter, various information concerning the customer/patient may be collected and used. The security and privacy of such information is managed in the operation of the pharmacy management system when a signature capture device is used to display and capture personal information of the customer.

Specific embodiments of the invention involve the display of targeted messages at the signature capture device in response to the processing of a prescription for pickup by a customer. A targeted message is identified for display in response to the receipt of a prescription identification, such as by scanning a barcode on a pharmaceutical item being purchased by the customer. The prescription identification is used to identify and retrieve predefined criteria from a pharmacy dispensing database, where the criteria relate to attributes of the prescribed item and/or attributes of the patient. For example, the criteria may include, among other things, the age of the patient, gender of the patient, the type of medication being prescribed, and past history of the prescription (last fill date, original fill date, etc.). The predefined criteria is used to query a message rules database to identify the targeted message. The identified targeted message is then retrieved from a message screen/content database, and provided for display at the signature capture device. Data from the message and customer responses to the message may be stored in a logging database at the pharmacy system.

Various types of messages can be displayed, such as an educational message concerning the particular prescribed medication, a message concerning alternative medications that may be substituted for the prescribed medication, supplemental medications or other items that can be used in conjunction with the prescribed medication, and the existence of studies related to the pharmaceutical prescription or that may be determined to be of interest to the customer. In many cases, the targeted message may require a response from the customer/patient.

In embodiments of the invention, information that may be of a personal nature might be used, and such information is managed to preserve its security and privacy. For example, personal identification of the customer is not included in the predefined criteria provided in response to the prescription identification—to avoid that identifying information being used, stored, displayed or made available in conjunction with the targeted message, and thus being made accessible to pharmacy employees or other customers during the messaging process. Further, if a customer response to a targeted message is stored (e.g., a response that may identify the patient or attributes of the patient) the response is encrypted and de-identified when stored, again to avoid personal information of the customer being made accessible to pharmacy employees or other customers as a result of the messaging process. As an example, a response may be de-identified by removing any information associated with the response that might identify the customer, such as a name, personal identifier, Social Security number, etc. Thus, the pharmacy management system performs operations to minimize the collection and propagation of personal information within the pharmacy management system that may result from the display and use of targeted messages, including personal information retrieved from the pharmacy dispensing database, messages displayed at the signature capture device, and data stored in the logging database at the pharmacy system.

Further, when a targeted message is displayed, and a customer response is not received (or other action taken by the customer) within a specified period of time, the message may be removed from the display, in order to avoid another person (such as a subsequent customer who approaches the pharmacy counter) seeing the display and obtaining or inferring personal information relating to the previous customer (such as messages pertinent to the medication or a condition being treated).

As should be appreciated, pharmacies desire to take steps to prevent the unnecessary collection, disclosure or propagation of personal information of its customers. Such steps add to the complexity and cost of pharmacy systems and software. Embodiments of the invention reduce the opportunity for such personal information being collected, stored or made accessible (inadvertently or otherwise) as part of the operation of a pharmacy management system and signature capture/display device, and thus improve the cost, operation and complexity of those systems and devices.

An overall environment in which the present invention may be used is similar to that described in co-pending U.S. application Ser. No. 13/102,570, filed May 6, 2011, for "Methods, Systems And Computer Program Products for Providing Targeted Displays for Pharmacy Signature Capture Systems," which application is hereby incorporated by reference for all purposes herein.

FIG. 1 is a block diagram of a pharmacy management system 100, according to some embodiments of the invention. As shown in FIG. 1, the pharmacy management system 100 includes a controller 110, a targeted message module 140, a database 150 and a signature capture system/device 170. A pharmacy dispensing module 130, an Interactive Voice Response (IVR) system 120 and/or other pharmacy management modules 180 also may be included. The controller 110 may be embodied as one or more enterprise, application, personal and/or pervasive computer systems which may be connected by a network such as a local area network and/or a wide area network including the Internet. The controller 110 can coordinate interaction among the other components of FIG. 1. It will be understood that the functionality of the controller 110 can be centralized and/or distributed among the other components.

The IVR system components 120 may be coupled to one or more telephone lines to receive telephone calls from callers. The IVR system 120 can include prerecorded voice prompts such as prerecorded human voice segments, stored text-to-speech generated segments, text-to-speech segments that are generated on the fly, for voice prompts. The pharmacy dispensing system 130 may be used to manage patient records, manage doctor records, manage medication data, facilitate prescription fulfillment and/or perform other functions. Other pharmacy management systems 180 may be used to perform other pharmacy management functions.

Other details concerning the design and operation of the IVR system 120, pharmacy dispensing system 130 and other pharmacy management systems 180 are described in U.S. Pat. No. 7,558,380, to DiVenuta et al., which is incorporated herein by reference in its entirety. Moreover, it will be understood that the IVR system 120, the pharmacy dispensing system 130 and/or the other pharmacy management systems 180 may be combined to run on a single enterprise, application and/or personal computer system. Alternatively, these systems may be distributed over more than one enterprise, application, personal and/or pervasive computer systems which may be connected by a network such as a local network and/or a wide area network including the Internet.

Still referring to FIG. 1, a pharmacist terminal 190 may be used by a pharmacist to perform pharmacist functions in the pharmacy. A barcode scanner 192 also may be included and may be used by the pharmacist to identify a pharmaceutical prescription by scanning a barcode on a container (a bag, box, bottle, etc.) that corresponds to the pharmaceutical prescription. The design and operation of a barcode system, such as could be used in connection with improvements to pharmacy systems as implemented by the present invention, is described in various prior patents, for example, U.S. Pat. No. 8,567,680, to Roquemore III et al., which is incorporated herein by reference in its entirety.

Still referring to FIG. 1, a targeted message module 140 is provided according to some embodiments of the present invention. The targeted message module 140 may comprise hardware and/or software. The targeted message module 140 is configured to identify a targeted message for displaying on the signature capture system 170 using predefined criteria that are based on an identification of a pharmaceutical prescription. The predefined criteria for identifying a targeted message may be stored in at least one database 150 as will be described in detail below. It will be understood by those having skill in the art that the targeted message module 140 and/or database 150 may be integrated within one or more of the other components of the pharmacy system 100, in some embodiments. In other embodiments, the targeted message module 140 and/or database 150 may be provided on one or more enterprise, application, personal and/or pervasive computer systems that may be connected to one another using a network such as a local area network and/or a wide area network including the Internet. It will be understood by those having skill in the art that the term "database" is used herein to generically represent any kind of querying system, such as a rules engine, table, neural network, etc.

The signature capture system 170 may include one or more touch screen displays that are configured to accept a signature using a stylus and/or other device and may also include one or more keys and/or buttons (fixed and/or programmable) that may be activated by a user, for example, using a stylus and/or finger, to provide various user inputs. Various sequences of display screens may be displayed and user inputs may be accepted to provide prompt/response and/or information to a user of the signature capture system. The overall design of a signature capture system, as could be used in connection with improvements to pharmacy systems as implemented by the present invention, is described in various prior patents, for example, U.S. Pat. No. 8,588,483, to Hicks et al., which is incorporated herein by reference in its entirety.

Pharmacy operating systems, methods and/or computer program products according to some embodiments of the present invention may operate in response to accepting a signature on a signature capture system, such as the signature capture system 170 of FIG. 1, during a pharmacy transaction. A targeted message is identified, for example by the targeted message system 140, for display on the signature capture system 170, using predefined criteria that are based on an identification of a pharmaceutical prescription that is associated with the signature that is accepted. Accordingly, a point-of-signature capture may be used to provide targeted message displays to the user who is providing a signature, also referred to herein as a "signor".

Systems, methods and/or computer program products according to embodiments of the present invention can provide the pharmacy and/or other interested parties an ability to display targeted informational messages, targeted promotional messages, targeted surveys and/or other targeted messages to users who are providing a signature during a pharmacy transaction. In some embodiments, a targeted message may be identified for displaying to the user using predefined criteria that are based on identification of the pharmaceutical prescription related to the user. In some embodiments, the pharmacy system may have access to specific patient data through the pharmacy dispensing system 130, based on the identification of the pharmaceutical prescription. Using this data, the targeted message module 140 may retrieve various predefined identifiers that indicate signors as candidates for display of a specific targeted message that may directly relate to their prescription. If a patient meets a set of identified criteria that matches a targeted message, the targeted message module 140 can display the message(s) and gather any responses through the signature capture system 170. It will be understood by those having skill in the art that a message can include a single displayed message, a series of displayed messages, or a complex message flow.

Figure 2:
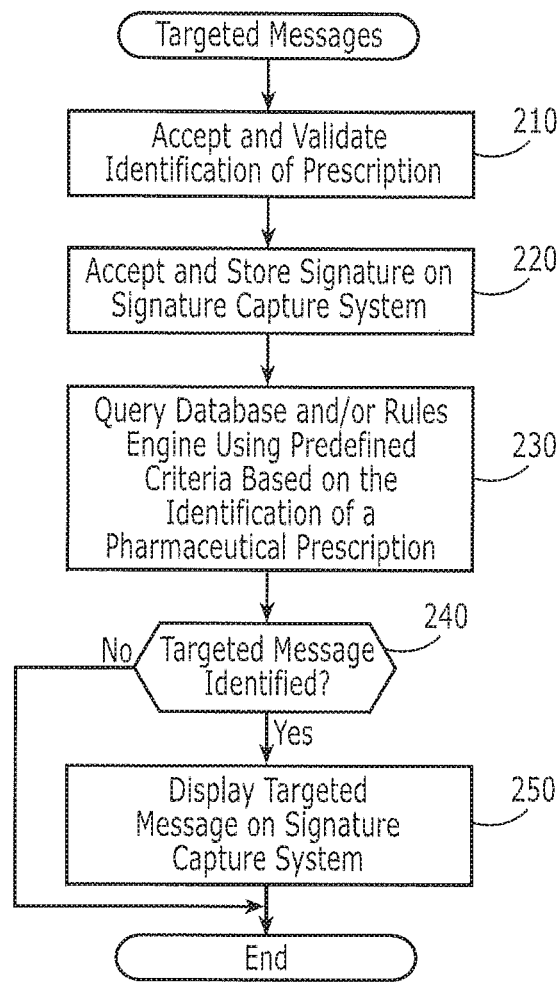
FIGS. 2 and 3 are flowcharts of operations that may be performed to provide targeted messages according to some embodiments of the present invention.

FIG. 2 is a flowchart of operations that may be performed to provide targeted messages according to some embodiments of the present invention. These operations may be provided, for example, by the targeted message module 140 of FIG. 1, using the signature capture system 170 and/or other components of FIG. 1.

Referring now to FIG. 2, at Block 210, an identification of a pharmaceutical prescription is accepted during a pharmacy transaction. The identification of a pharmaceutical prescription generally is a prescription number ("Rx number") which may be provided at various times during the pharmacy transaction. For example, when the prescription is being filled, a barcode scan of a barcode on a container that corresponds to the pharmaceutical prescription may be accepted. The barcode scan may be performed by a pharmacist, a pharmacy clerk and/or other employee using the pharmacist terminal 190 and/or barcode scanner 192. Alternatively, at various points during the pharmacy transaction, the pharmaceutical prescription number (Rx number) may itself be input by a pharmacist and/or clerk using a keyboard and/or other input device at the pharmacist terminal 190 and/or another terminal. In still other embodiments, the pharmaceutical prescription number itself is not directly input but rather identification information such as the patient's last name is input, which can be used to identify the pharmaceutical prescription as part of the pharmacy transaction. In some embodiments, the identification of the prescription may be validated, such as by verifying the format, e.g., verifying the proper number of characters.

Still referring to FIG. 2, at Block 220, a signature is accepted on a signature capture system during the pharmacy transaction. The signature may be accepted at one or more points during the pharmacy transaction. For example, a signature may be accepted to acknowledge receipt of the pharmaceutical prescription, to acknowledge HIPPA information receipt and/or to confirm credit card/debit card payment. In other embodiments the signature may be accepted as part of a prompt asking the user as to whether the user desires to receive a targeted message. More than one signature may be accepted. The captured signature may be stored for archival purposes, such as by storing in the logging database 154. Moreover, it will also be understood that the operations of Blocks 210 and 220 may be performed in the order shown in FIG. 2, at least partially concurrently, or the operations of Block 210 may be performed at least partially after a signature capture of Block 220.

It will also be understood that the signor of the signature capture system may be the patient (i.e., the user of the medication of the pharmaceutical prescription) or the signor may be someone who is signing on behalf of the patient such as a relative or friend of the patient.

Still referring to FIG. 2, at Block 230, at least one database, such as a database 150 of FIG. 1 and/or a database in the pharmacy dispensing system 130, is queried using predefined criteria based on the identification of a pharmaceutical prescription, to identify a targeted message. It will be understood by those having skill in the art that the term "database" is used herein to generically represent any kind of querying system, such as a rules engine, table, neural network, etc. In some embodiments, the predefined criteria based on identification of a pharmaceutical prescription can comprise age of the patient, gender of the patient, medication of the pharmaceutical prescription, last fill date of the pharmaceutical prescription, days supply on last fill of the pharmaceutical prescription, original fill date of the pharmaceutical prescription, disease state of the patient, physician of the patient and/or other promotions in effect. In other embodiments, the predefined criteria based on identification of a pharmaceutical prescription do not provide a personal identification of the patient for privacy and/or other reasons. In some embodiments, at least one pharmacy dispensing system database, such as at least one database in the pharmacy dispensing system 130, is queried using the identification of the pharmaceutical prescription to identify the predetermined criteria. Then, at least one message database, such as at least one database 150 that is associated with the targeted message module 140, is queried using the predetermined criteria to identify a targeted message to be displayed. It will also be understood that the operations of Block 230 may be performed prior to, at least partially simultaneous with and/or after the operations that are performed at Block 220.

Still referring to FIG. 2, at Block 240, if a targeted message is identified, then the targeted message is displayed on the signature capture system, at Block 250. In some embodiments, prior to displaying the targeted message, an "opt-in" message is displayed, asking whether the patient wishes to opt-in to hear an informational, educational, clinical research study opportunity, etc., message, and upon acceptance, the targeted message is displayed. More specifically, in some embodiments, at Block 240, a targeted message that corresponds to the age of the patient, gender of the patient, medication of the pharmaceutical prescription, last fill date of the pharmaceutical prescription, days supply on last fill of the pharmaceutical prescription, original fill date of the pharmaceutical prescription, disease state of the patient, physician of the patient and/or other promotions in effect, is identified based in the database query. In some embodiments, the targeted message may comprise an educational message concerning the pharmaceutical prescription, a message that indicates alternative medications that may be substituted for the pharmaceutical prescription, a message that identifies other items (related and/or unrelated to the pharmaceutical prescription) that may be desired by the patient and/or a message that solicits participation of the patient in a study related to the pharmaceutical prescription.

The targeted message may be displayed on a signature capture system at Block 250 using many different techniques. For example, some signature capture systems include a signature capture touch screen, and the targeted message is displayed on the signature capture touch screen. An enlarged touch screen may be provided in some embodiments so as to allow an enlarged display of targeted messages. In other embodiments, the signature capture system may include a separate instruction display that may be used to provide instructions for capturing a signature. In these embodiments, the targeted message may be displayed on the signature capture touch screen and/or the instruction display.

Many examples of targeted messages may be provided according to various embodiments of the present invention. For example, a targeted message may include text images (static or moving) in a single display or a series of screen displays. Indeed, any type of multimedia (audio and/or video) message may be displayed on the signature capture system to provide a targeted message to the signor. It will be understood that, in some embodiments, an audio message is not provided along with a displayed message for privacy purposes. From the perspective of the signor, some embodiments of the present invention display a targeted message at Block 250 in response to the signor providing a signature at the signature capture system. Accordingly, the functionality of the signature capture system may be expanded from merely accepting a signature and/or other rudimentary user inputs to providing targeted messages to the user.

Examples of criteria, targeted messages and their generation according to some embodiments of the present invention, will be described in detail below. However, it will be understood by those having skill in the art that these examples of criteria and targeted messages are only exemplary and many other criteria and/or targeted messages may be generated and used according to other embodiments of the present invention.

Figure 3:
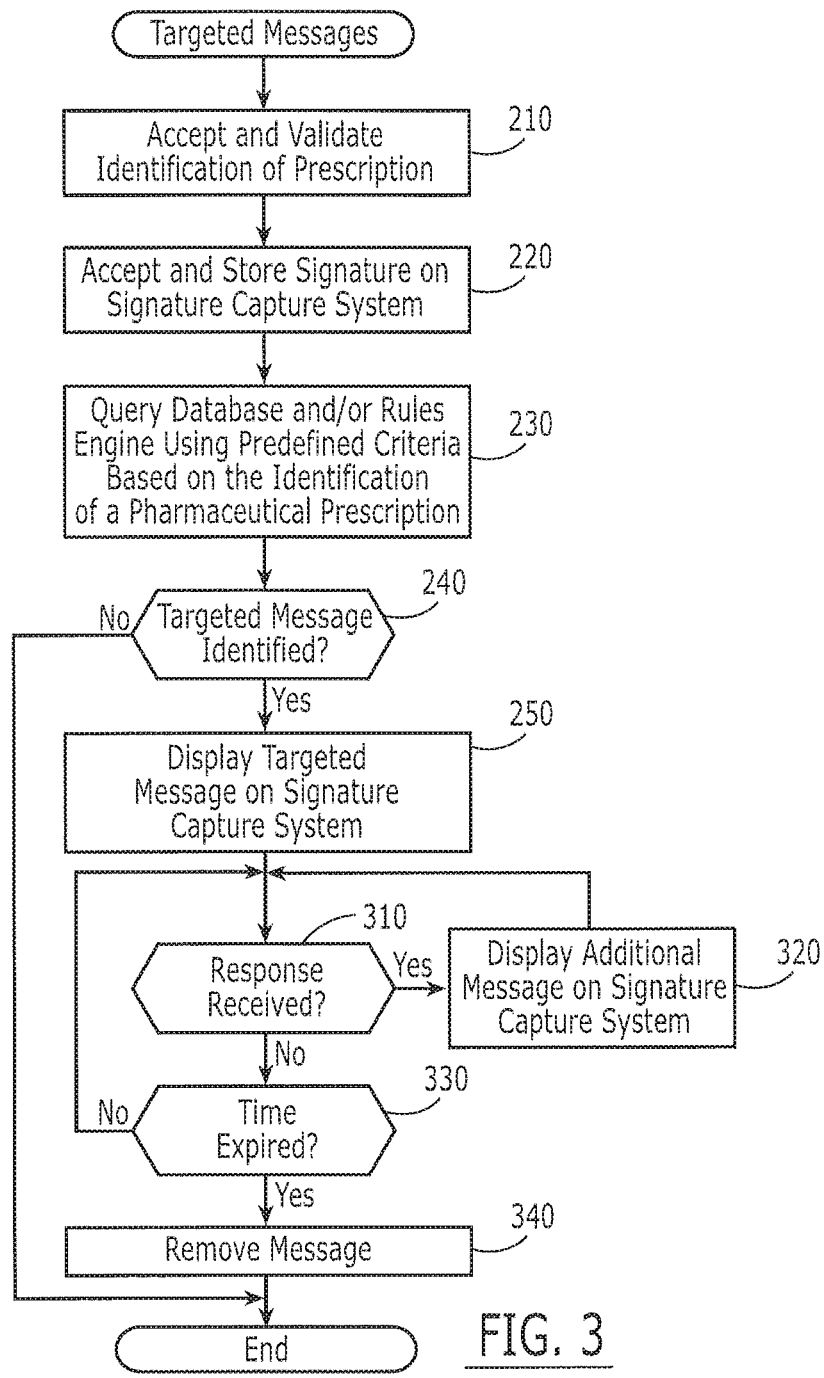

FIG. 3 illustrates operations that may be performed according to other embodiments of the present invention. In FIG. 3, the operations of Blocks 210, 220, 230, 240 and 250 are performed. Then, at Block 310 a test is made as to whether a response is received to the displayed targeted message of Block 250. A response may be received by providing a user input on the signature capture touch screen, on an associated keyboard, voice response system and/or other user input system that is associated with the signature capture system. If a response is received at Block 310, then at Block 320 additional targeted messages may be displayed on the signature capture system. The additional message may have all of the characteristics of the original message that were described above in connection with Block 250.

Still referring to FIG. 3, if a response is not received at Block 310 and a timer has expired at Block 330 then the message may be removed at Block 340. The message may be removed after expiration of a timer for privacy purposes. In some embodiments, after removing the message, a screen saver is displayed.

Figure 4B:
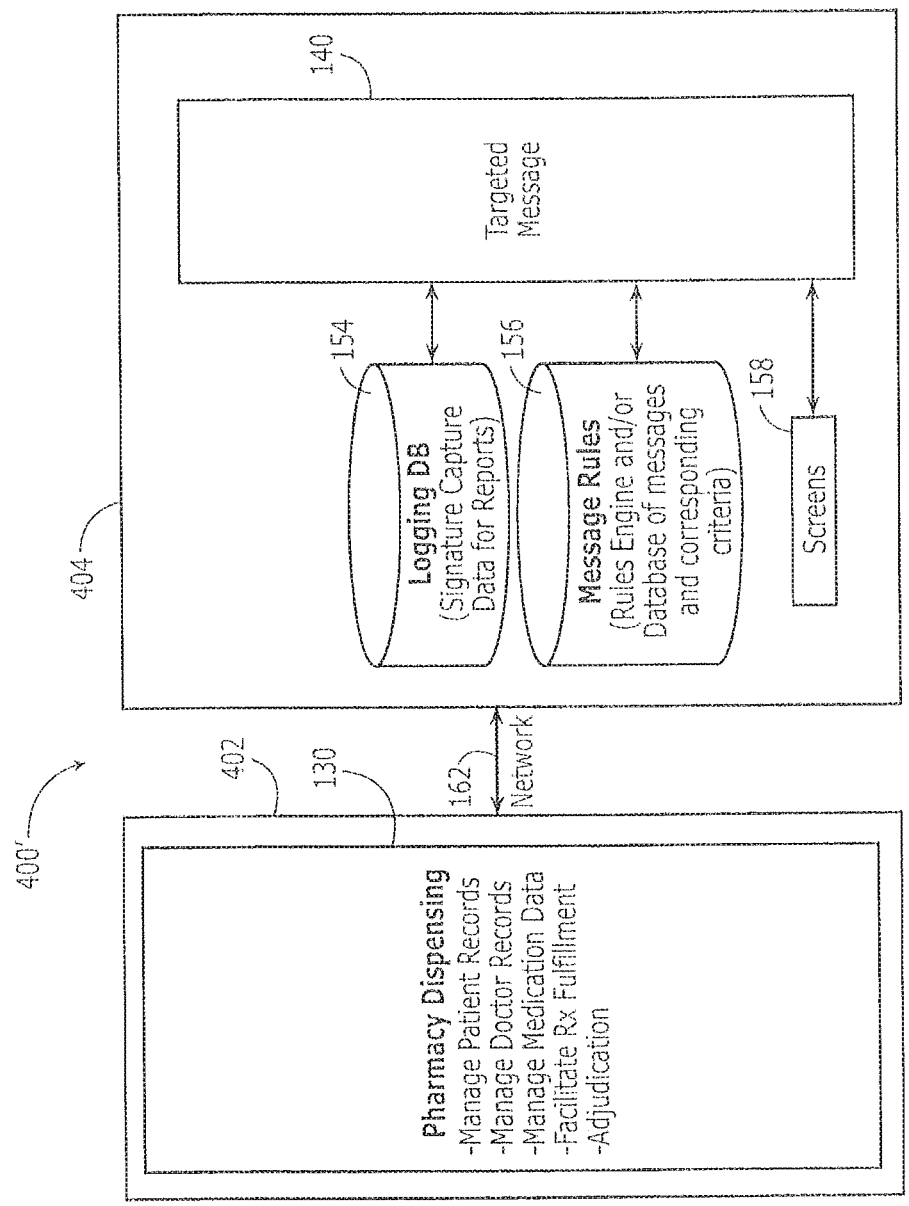

FIGS. 4A and 4B are detailed block diagrams of systems, methods and/or computer program products for providing targeted messages on a pharmacy signature capture system according to other embodiments of the present invention. In FIG. 4A, the pharmacy dispensing system 130 and targeted message system 140 are both included in a single data processing system 400, which may include one or more enterprise, application, personal and/or pervasive computer systems. The targeted message system 140 and the pharmacy dispensing system 130 may be connected by an internal hardware and/or software interface 160. In contrast, in FIG. 4B, the pharmacy dispensing system 130 is contained in a first data processing system 402, and the targeted message system 140 is contained in a second data processing system 404 that are connected by a network 162, which may include a local and/or wide area network including the Internet. Each of the first and second data processing systems 402 and 404, respectively, may include one or more enterprise, application, personal and/or pervasive computer systems.

Still referring to FIGS. 4A and 4B, the pharmacy dispensing system 130 can include functionality for managing patient records, managing doctor records, managing medication data, facilitating prescription (Rx) fulfillment and/or adjudication between the pharmacy and the payer (insurance company). A plurality of databases are shown in FIGS. 4A and 4B. In particular, a logging database 154 may log data and/or other events for reports. A message rules database 156 can store therein messages and corresponding criteria that can trigger a message. It will be understood by those having skill in the art that the term "database" is used herein to generically represent any kind of querying system, such as a rules engine, table, neural network, etc. Finally, a screens database 158 can store therein actual screen images (static and/or moving) that are used for the messages. It will be understood that some or all of the functionality of databases 154-158 may be combined into one or more databases, which may correspond, for example, to the database 150 of FIG. 1. Accordingly, as used herein, a database includes a centralized and/or distributed database.

Figure 5A:
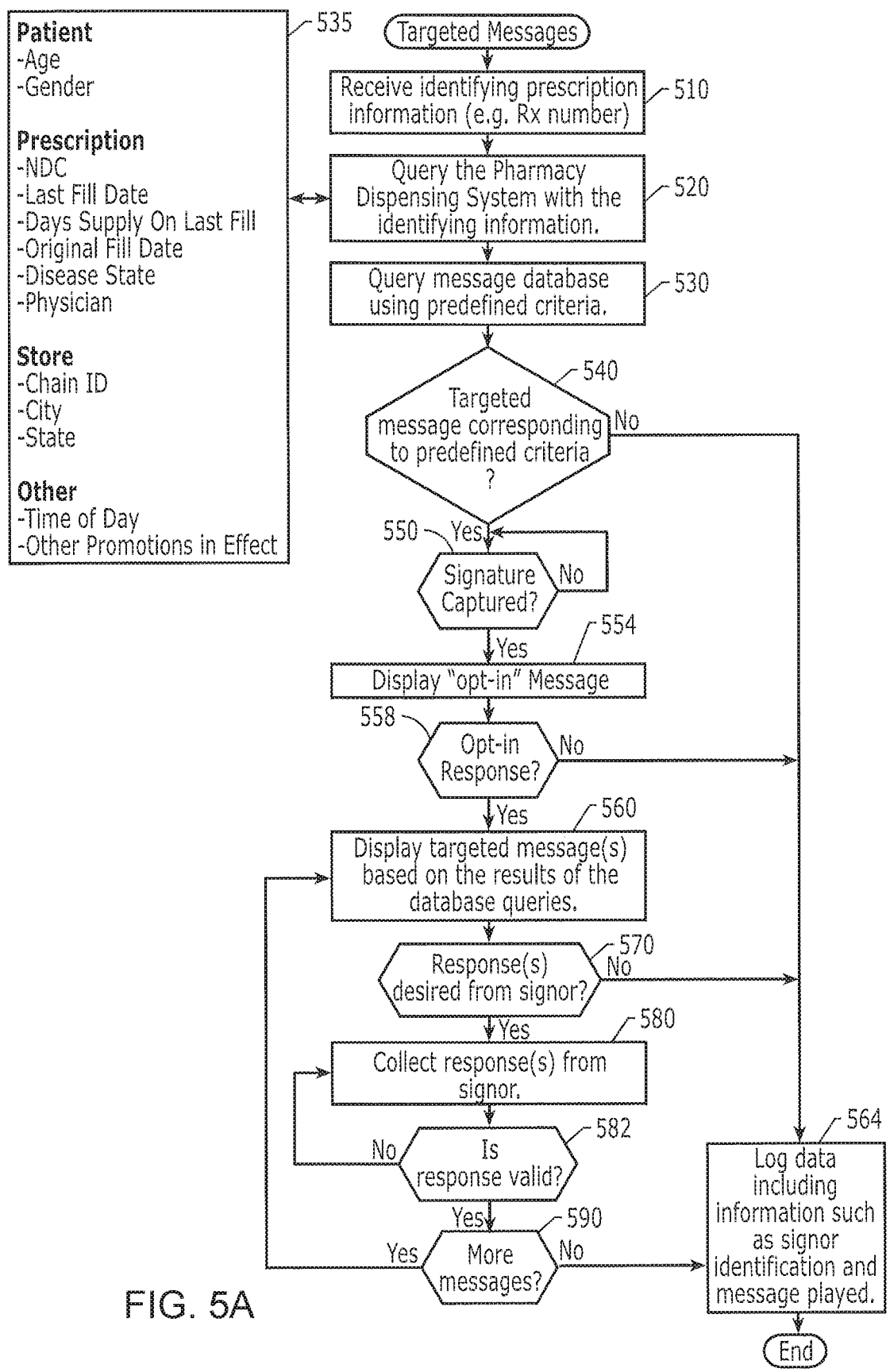
FIG. 5A is a flowchart of operations that may be performed to provide targeted messages according to some embodiments of the present invention.

FIG. 5A is a flowchart of operations that may be performed to provide targeted messages according to some embodiments of the present invention. In particular, referring to FIG. 5A, at Block 510, the identifying prescription information is received at some point during the pharmacy transaction. As was described above, the identification of a pharmaceutical prescription may be received via a barcode scan at the time the prescription is dispensed and/or at another time, by input of a prescription number by a pharmacist and/or clerk and/or by accepting input of identification information, such as last name, that can be used to identify the pharmaceutical prescription as part of the pharmacy transaction. Then, at Block 520, the pharmacy dispensing system is queried with the identifying information (e.g., pharmaceutical prescription number). As shown at Block 535, the pharmacy dispensing system and/or other system may include one or more patient databases that may include patient age and patient gender. One or more prescription databases may also include information about the pharmaceutical prescription, such as the National Drug Code (NDC) (i.e., the medication of the pharmaceutical prescription), last fill date, days supply on last fill, original fill date, disease state and physician. One or more store databases may also include information on the pharmacy itself, such as a chain ID, city and state. Other databases may include time of day and other promotions that are in effect. It will be understood that combinations and subcombinations of these databases may be merged into one or more databases. Moreover, not all of the fields need be included in the database and/or one or more of the fields may be inferred from other fields. For example, the gender of the patient may be inferred from the medication that is identified. Similarly, a disease state may be inferred from the medication that is identified. At Block 530, the prescription number or other entered information is used to identify predetermined criteria related to the patient or the patient's medication. It will be understood that, in some embodiments, the actual identity of the patient need not be provided, but only information concerning the patient/medication may be identified.

Then, at Block 540, the information that was obtained is compared with a message database, such as a message rules database 156 of FIGS. 4A and 4B, in order to determine which targeted messages may be pertinent and which messages to display. At Block 550, if a targeted message corresponds to, e.g., matches, the predefined criteria based on the prescription number, then at signature capture time during the transaction, targeted messages are displayed based on the results of the database queries. This message is targeted in that it can directly address specific needs or conditions of the user.

If a targeted message corresponding to the predefined criteria is not found at Block 540, then the operations may be continued at Block 564, to log data and/or selected data. Logging may be performed for reporting and/or analysis. Logging data may include identification/attributes of the user, messages displayed, date and time, user responses, etc.

Returning to Block 550, if a targeted message is identified at Block 540, a display of a "opt-in" message is provided at Block 554. The display may be an "Opt-In" button and/or a message that indicates a choice of opting in to see the subsequent message. At Block 558, if "Opt-In" is selected, then the targeted messages are displayed, simultaneous with, prior to, and/or after signature capture based on the results of the database queries, at Block 560. If a response is desired from the signor at Block 570, then one or more responses are collected from the signor at Block 580, with standard or other tests being made at Block 582 to validate responses. A response may be desired at Block 570, for example, if the signor is given the option to switch to a different medication or is offered the opportunity to complete a customer survey. A response may be checked for validity at Block 582 by verifying the proper format, e.g., proper number of characters, and/or performing other validation tests.

Finally, at Block 590, if more messages are available, the user is returned to the message portion of the flow (Block 560). If the messages and/or customer action is complete, at Block 590, the messages/responses may be logged at Block 564 and operations can end. It thus will be understood that a single targeted message, a series of related targeted messages or a plurality of unrelated targeted messages may be displayed according to various embodiments of the invention.

Figure 6:
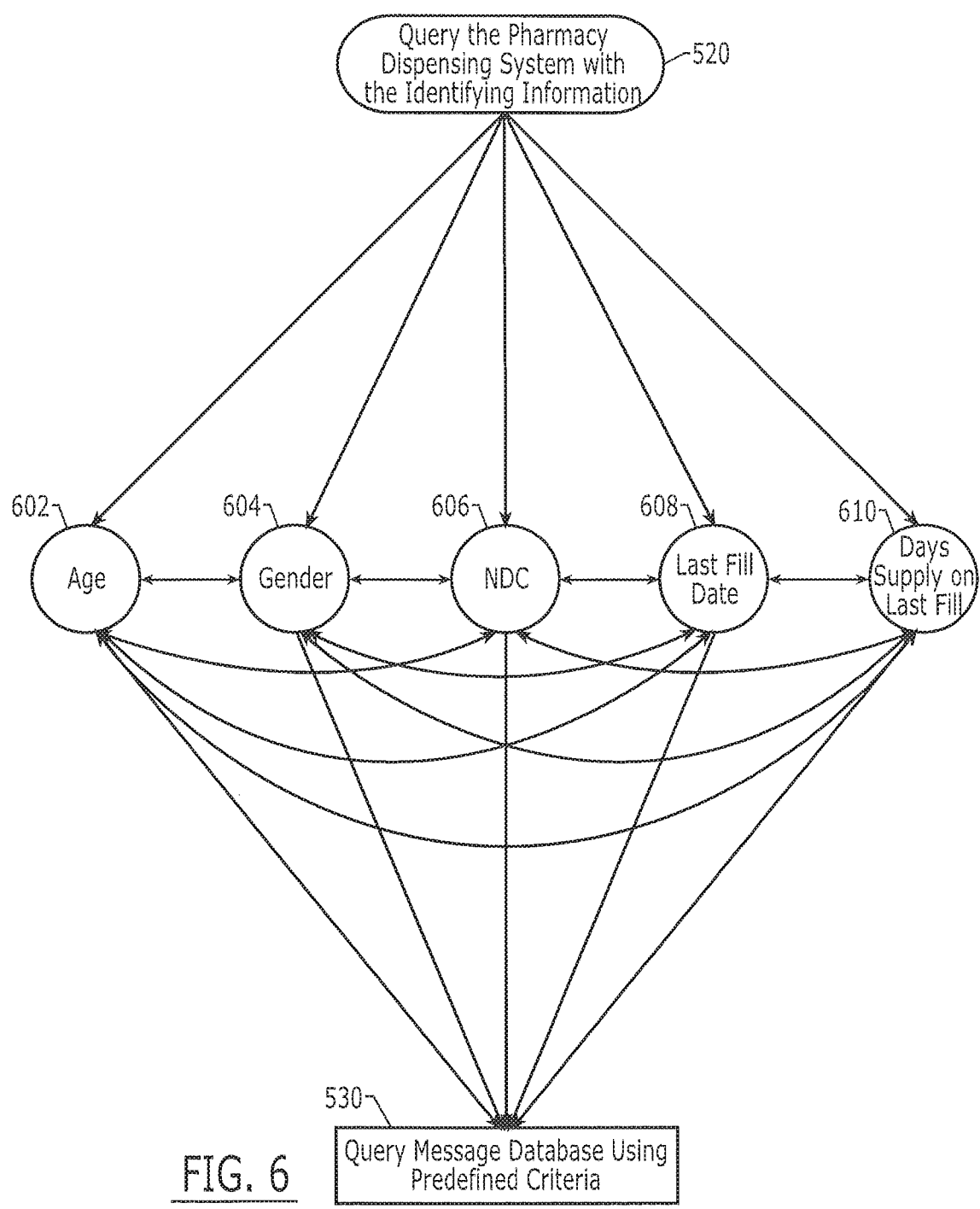
FIGS. 6 and 7 are flowcharts that illustrate various combinations of predetermined criteria that may be used to identify targeted messages according to various embodiments of the present invention.
Figure 7:
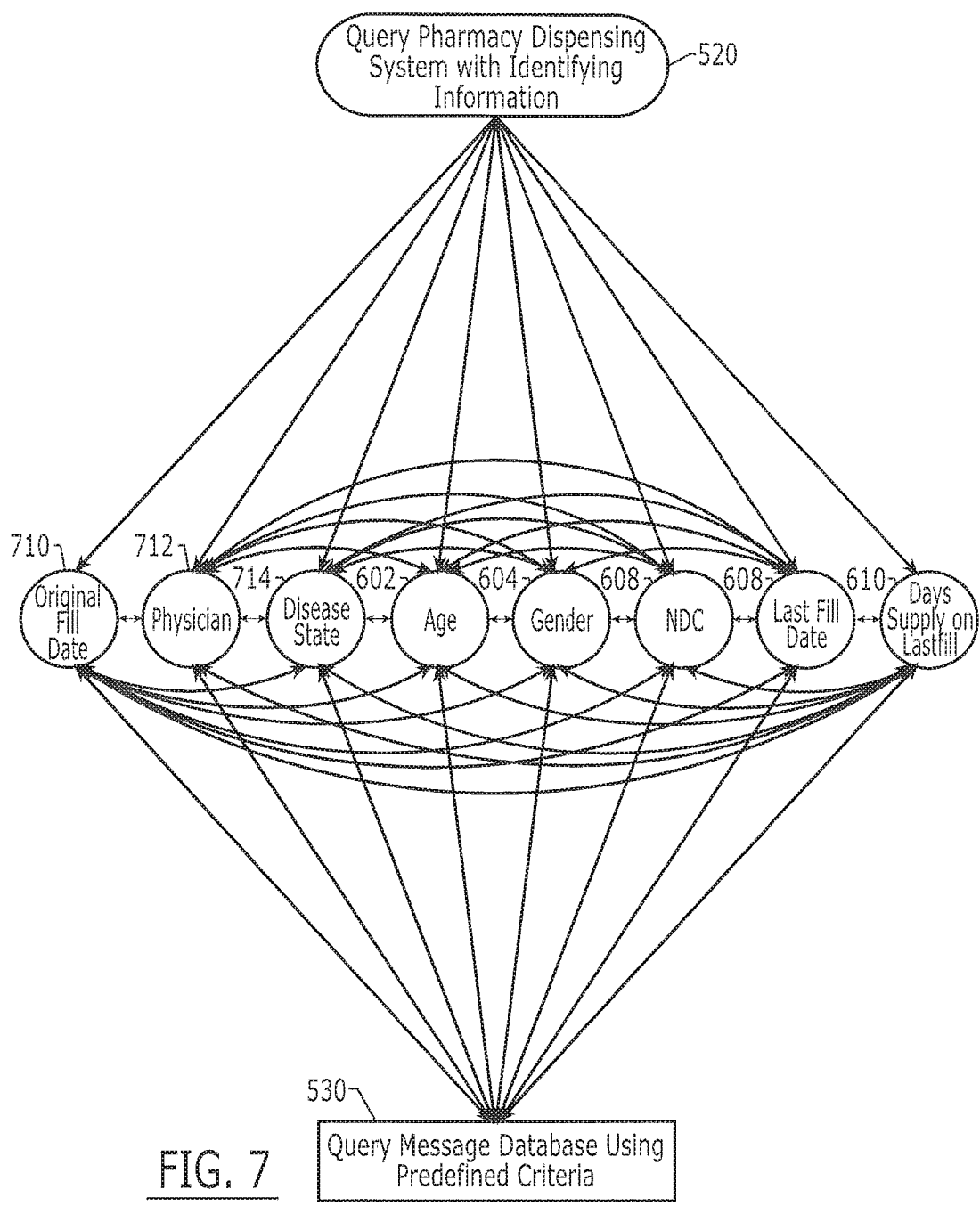

Returning again to FIG. 5A, at Block 540, many types of predefined criteria may be used to query at least one database based on the identification of a pharmaceutical prescription, to thereby identify a targeted message to be displayed. In some embodiments, combinations and subcombinations of five criteria may be queried. In particular, as shown in FIG. 6, age 602, gender 604, NDC (medication) 606, last fill date 608 and/or days supply on last fill 610 may be queried in order to query at least one database using predefined criteria at Block 530. In some embodiments, the business rules can represent multiple qualifying and/or disqualifying NDCs 606. For example, if a diabetic patient is taking Glucophage (metformin hydrochloride) and Lantis (insulin), then display a given targeted message. Moreover, gender 604 may be inferred. Other criteria, such as zip code or location, also may be used. FIG. 7 illustrates eight criteria including combinations and subcombinations of original fill date 710, physician 712 and disease state 714, in addition to criteria 602-610 of FIG. 6, which may be used to query at least one database using the predefined criteria at Block 530. A co-morbidity qualifier also may be provided, in addition to, or instead of disease state 714, in some embodiments. Other combinations and subcombinations of these and/or other criteria may be used.

Figure 5B:
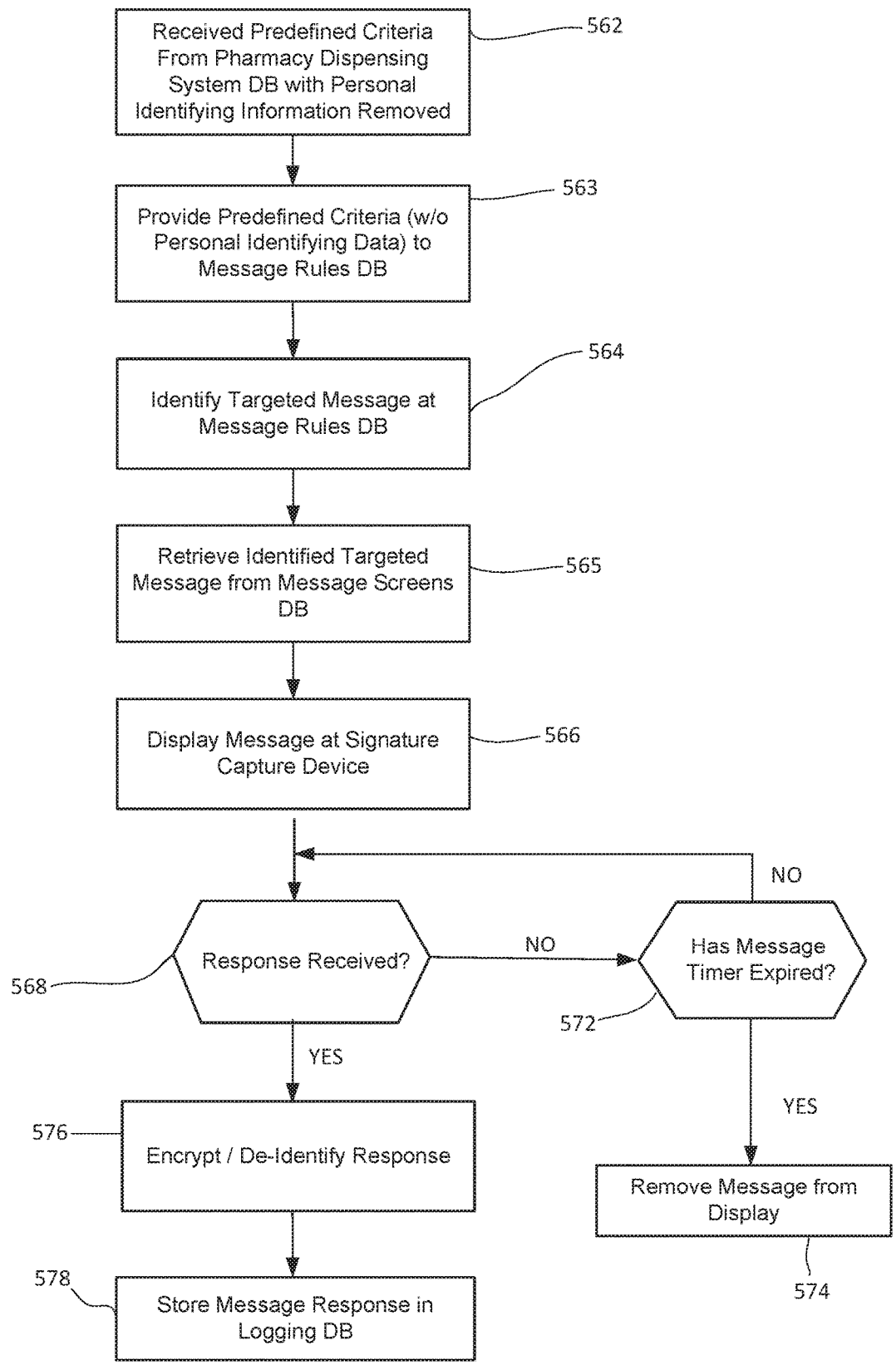
FIG. 5B is a flow chart illustrating some of the operations seen in FIG. 5A, but with further detail concerning the management of personal information of a customer that may be used when selecting or displaying a targeted message.

FIG. 5B is a flow chart of operations that may be performed to provide targeted messages according to some embodiments of the invention, with further detail (over that seen in FIG. 5A) concerning the management of personal information of a customer that may be used when selecting or displaying a targeted message. Generally, and as was described earlier, the process carried out within the pharmacy management system 100 improves security by reducing/eliminating the use of personal identifying information when predefined criteria is retrieved from the databases in pharmacy dispensing system 130, removing messages from the display of the signature capture device after a pre-established period of time has expired (to avoid access to persons other than the customer to whom the message are targeted), and removing personal identifying data from any response received from a customer prior to the response being logged into the logging database 154.

Referring to FIG. 5B, when the patient databases within the pharmacy dispensing system 130 are accessed (step 535, FIG. 5A) using a prescription identifier, the predefined criteria is returned with personal identifying information from the patient database removed, step 562. For example, when patient or prescription data is retrieved, only non-identifying data (such as the age or gender of the patient, name of the prescribed item, etc.) is returned, without patient identifying data such as name, social security number, etc. As an example, the pharmacy dispensing system can be programmed to query the patient and prescription databases for predefined criteria that excludes customer identity information or other sensitive information, when the query is made in response to a barcode scan or other input made at the time of prescription pickup.

The predefined criteria (without personal identifying data) is then provided to the message rules database 156 as a query in order to identify a targeted message, step 563. Since no personal identifying message is present in the predefined criteria, the communications with the message rules database to identify the targeted message has little or no information that could be used to identify the customer. At step 564, the system retrieves the identified targeted message from the message screens database 158, and it is then displayed at the signature capture device, step 566. Since no personal identifying information has been involved in identifying the targeted message, the content provided through the system for display at the signature capture device likewise does not provide any personal identifying information.

In some embodiments, the message displayed at step 566 requests a response from the customer, for example, as mentioned earlier, asking whether the customer has an interest in educational information concerning the prescription, interest in alternative prescriptions or other medications, or interest in participating in a survey. To preserve the privacy of information in the message, the pharmacy system checks whether a response has been received, step 568, and if not, determines whether a predetermined time has expired for providing response, step 572. If the time has expired, the original message is removed from the display, step 574, so that, if the customer has left the pharmacy counter without responding, another customer will not see the message and any information pertaining to the customer that is contained in the message.

As a further feature for meeting the security and privacy of customer information contained in a response received at step 568, any identifying information that may be contained in the response is removed, step 576, before the response is stored in the logging database 154 at step 578. If the customer has entered personal information as part of requesting information on an alternative prescription or in participating (or expressing interest in participating) in a survey, that information may be removed from responses at step 576, either by deleting the information from the response when received at the logging database 154 or by encrypting that information before it is stored. As an example, if the customer expresses interest in alternative medication and requests to speak with a pharmacist, any indication in the response that there is an interest is removed before the response is logged (of course, any alternative prescription subsequently ordered would be processed and stored per normal procedures in the pharmacy dispensing system). As another example, if participation in a survey requires personal information (such as a name and address), such information may be sent to the administrator of the survey, but would not be stored in the logging database 154.

It should be appreciated that the foregoing steps relating to security and privacy reduce the opportunity for personal information be accessed as well as reduce system requirements that must be undertaken (for security) if such information is stored, for example, in the logging database.

FIGS. 8-11 provide examples of targeted messages that may be generated based on querying at least one database using predefined criteria based on the identification of a pharmaceutical prescription to identify a targeted message, according to some embodiments of the present invention. These examples are illustrative and shall not be construed as limiting. Operations of these Figures may correspond to Blocks 520-560 of FIG. 5A and/or Blocks 230-250 of FIGS. 2 and 3. In particular, FIG. 8 will describe educational messages concerning the pharmaceutical prescription, FIGS. 9A and 9B will describe targeted messages that indicate alternative medications that may be substituted for the pharmaceutical prescription ("switching"), FIG. 10 will describe a targeted message that identifies other (related and/or unrelated) items that may be desired ("upselling") and FIG. 11 will describe a targeted message that solicits participation in a study related to the pharmaceutical prescription ("research/survey"). Example display screens also will be provided.

Figure 8:
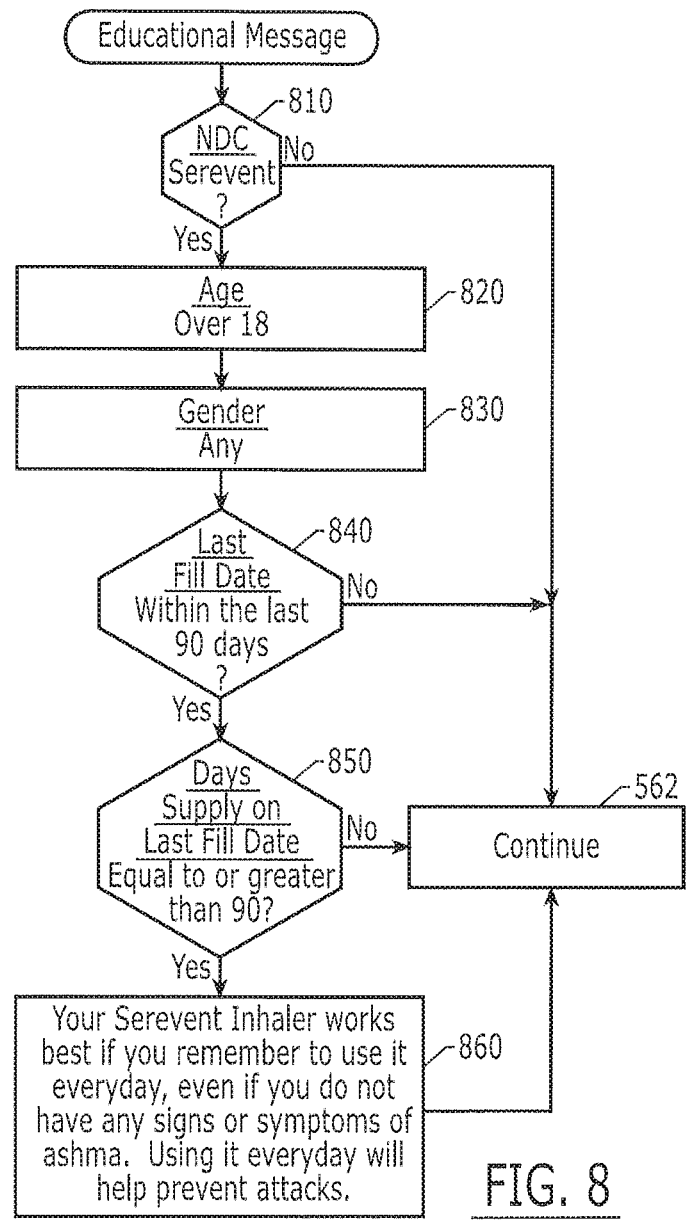
FIGS. 8-11 are flowcharts that illustrate examples of operations that may be performed to provide targeted messages according to various embodiments of the present invention.

Referring to FIG. 8, operations that may be performed to provide an educational message concerning the pharmaceutical prescription, according to some embodiments of the present invention, now will be described. As shown in FIG. 8, the following queries may be made to identify a targeted message matching the predefined criteria: At Block 810, a test is made as to whether the NDC (medication) corresponds to Serevent. If yes, at Block 820, age over 18, and at Block 830, any gender, may satisfy the criteria. At Block 840, a test is made as to whether the last fill date is within the last 90 days (or another first threshold) and at Block 850, a test is made as to whether the days supply on the last fill date is equal to or greater than 90 (or another second threshold which may or may not equal the first threshold).

If the tests of Blocks 810, 840 or 850 fail, then the operations continue at Block 562, including testing relative to other sets of predetermined criteria. However, if these tests pass, then a targeted message is displayed at Block 860 to display, "Your Serevent inhaler works best if you remember to use it every day, even if you do not have any signs or symptoms of asthma. Using it every day will help prevent attacks." Thus, in FIG. 8, if a sufficient number of days of supply of the medication remain, the user is reminded to take the medication every day. An educational message is thereby provided. Accordingly, FIG. 8 illustrates embodiments of the present invention wherein at least one database is queried using a predefined criteria of last fill date and days supply on last fill date, based on the identification of a pharmaceutical prescription and identifying an educational target message that reminds the patient how to use the pharmaceutical prescription if the last fill date is less than a first threshold and the days supply on last fill date exceeds a second threshold which may or may not equal the first threshold. It also will be understood that in other embodiments, other predefined criteria may be used to provide an educational targeted message related to the pharmaceutical prescription.

Figure 9A:
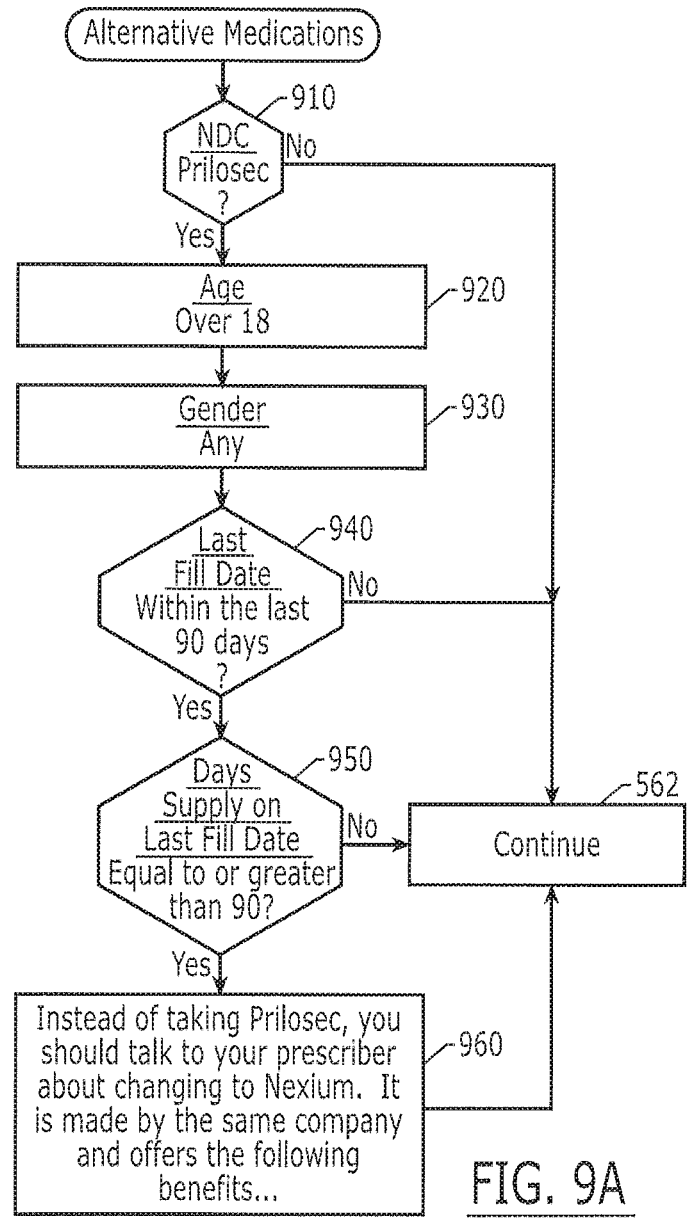
Figure 9B:
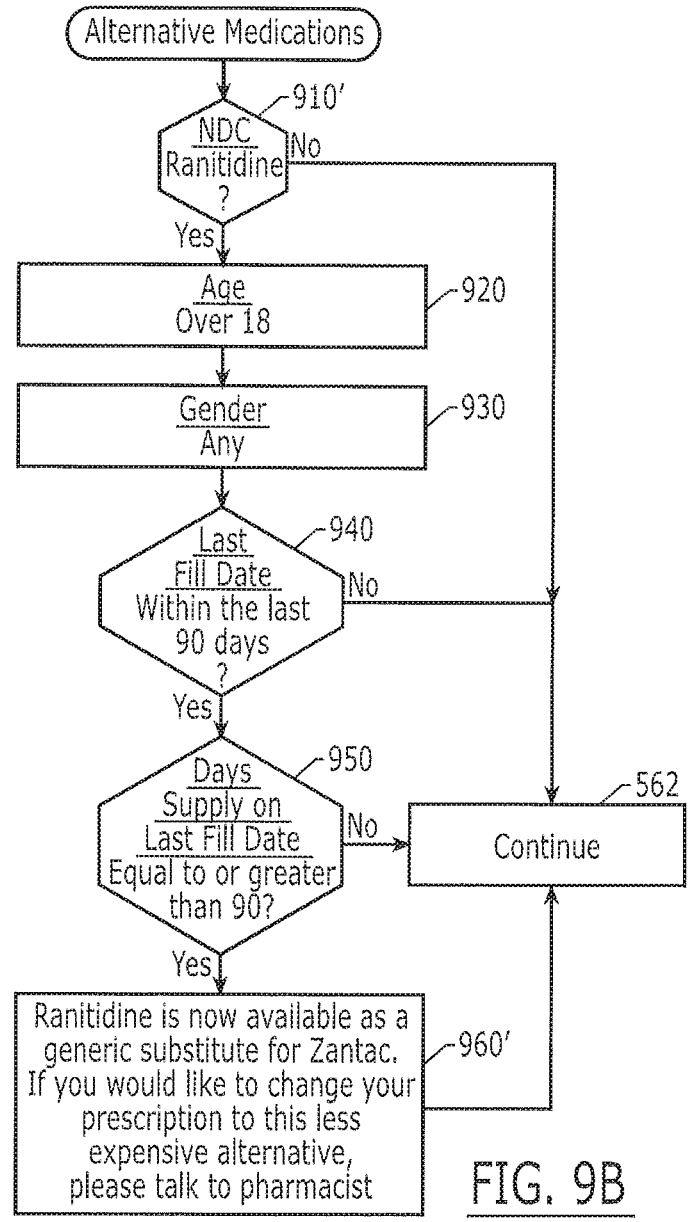

FIGS. 9A and 9B illustrate embodiments of the present invention, which can provide targeted messages that indicate alternative medications that may be substituted for the pharmaceutical prescription, i.e., a targeted message that can advise on switching to a different drug, also referred to as "brand transition". In particular, referring to FIG. 9A, at Block 910, a test is made as to whether the NDC is Prilosec. At Block 920, age over 18 may be identified and, at Block 930, any gender may be identified. At Block 940, if the last fill date is within the last 90 days and, at Block 950, if the days supply on the last fill date is equal to or greater than 90 days, then at Block 960, a message may be displayed that states, "Instead of taking Prilosec, you should talk to your prescriber about changing to Nexium. It is made by the same company and offers the following benefits . . . ." Alternatively, if the tests of Blocks 910, 940 and 950 are not satisfied, then the operations may be continued at Block 562.

FIG. 9B illustrates similar operations for the drug Ranitidine at Block 910'. At Block 960', a message may be displayed that, "Ranitidine is now available as a generic substitute for Zantac. If you would like to change your prescription to this less expensive alternative, please talk to the pharmacist." Accordingly, FIGS. 9A and 9B illustrate querying at least the database using predefined criteria of a last fill date and days supply on last fill date based on the identification of a pharmaceutical prescription, and identifying a targeted message that indicates alternative medications that may be substituted for the pharmaceutical prescription if the last fill date is less than a first threshold and the days supply on last fill date exceeds a second threshold, which may or may not be equal to the first threshold. It also will be understood that other predetermined criteria may be used to provide switching targeted messages, in other embodiments.

Figure 10:
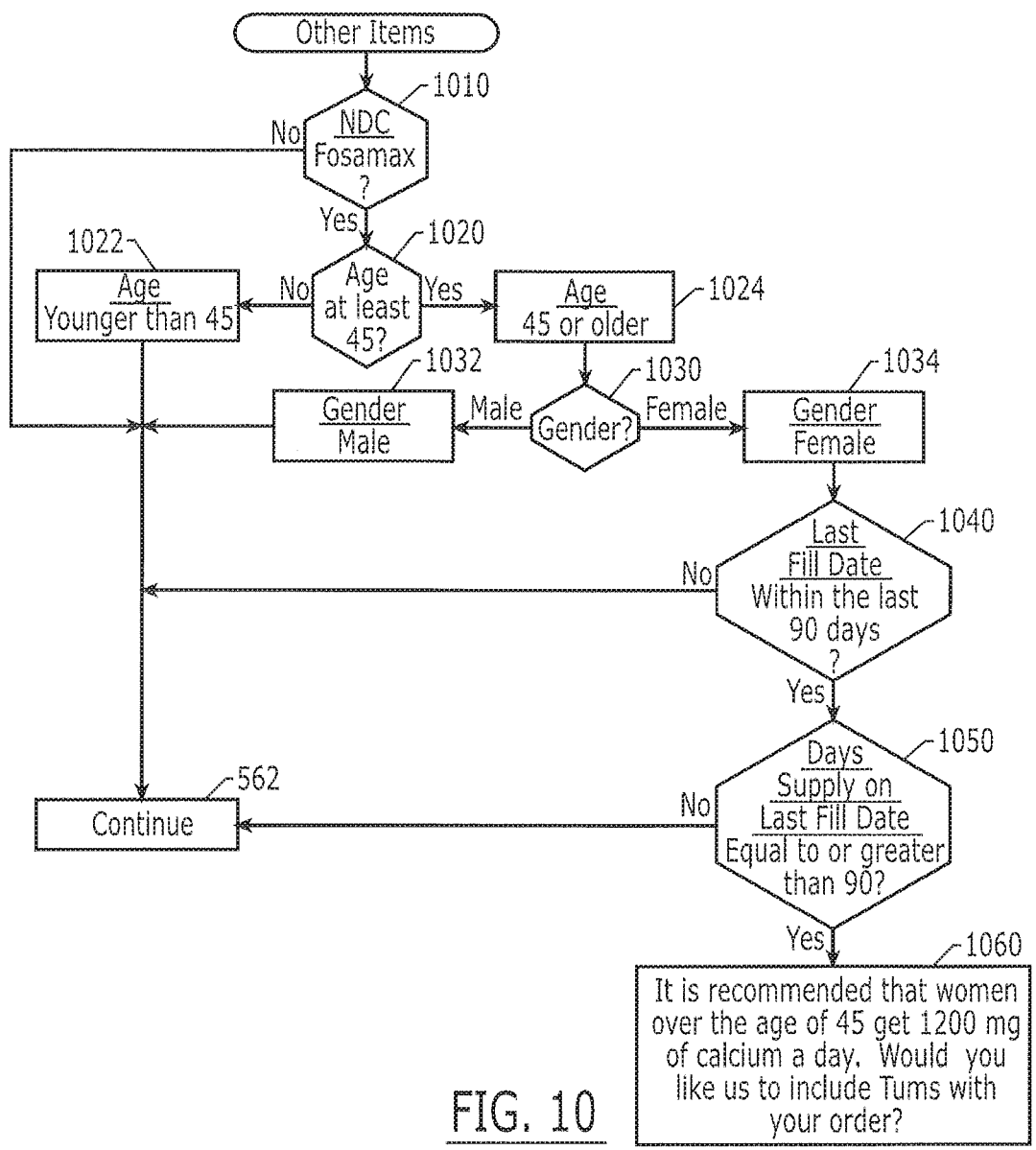

FIG. 10 is a flowchart of operations that may be performed to provide targeted messages regarding other items, also referred to as upselling, according to some embodiments of the present invention. The other items may include over-the-counter medications, supplies and/or other retail sales and add-on purchases, which may be related and/or unrelated to the prescribed product. At Block 1010, if the NDC (medication) is Fosamax, a test is made at Block 1020 as to whether age is at least 45. If the NDC is not Fosamax at Block 1010, or age is younger than 45 at Block 1022, then the prescription refill call flow may be continued at Block 562. However, if age is at least 45 at Block 1024, then at Block 1030, a test is made as to gender. If gender is male at Block 1032, then the prescription refill call flow may be continued at Block 562. However, if gender is female at Block 1034, then a test is made at Block 1040 as to whether the last fill date is within the last 90 days, and at Block 1050, as to whether the days supply on the last fill date is equal to or greater than 90 days. If these tests are passed, then at Block 1060, a targeted message is displayed stating, "It is recommended that women over the age of 45 get 1200 mg of calcium a day. Would you like us to include Tums with your order?". Accordingly, FIG. 10 illustrates embodiments of the present invention wherein if the gender is female, the age exceeds a first threshold, last fill date is less than a second threshold (which may or may not equal the first threshold) and days supply on the last fill date exceeds a third threshold (which may or may not equal the first and/or second thresholds), a targeted message is identified that indicates other items that may be desired. These embodiments can include a query of NDC, age, gender, last fill date and days supply on last fill date. It also will be understood that other predetermined criteria may be used to provide upselling targeted messages in other embodiments.

Figure 11:
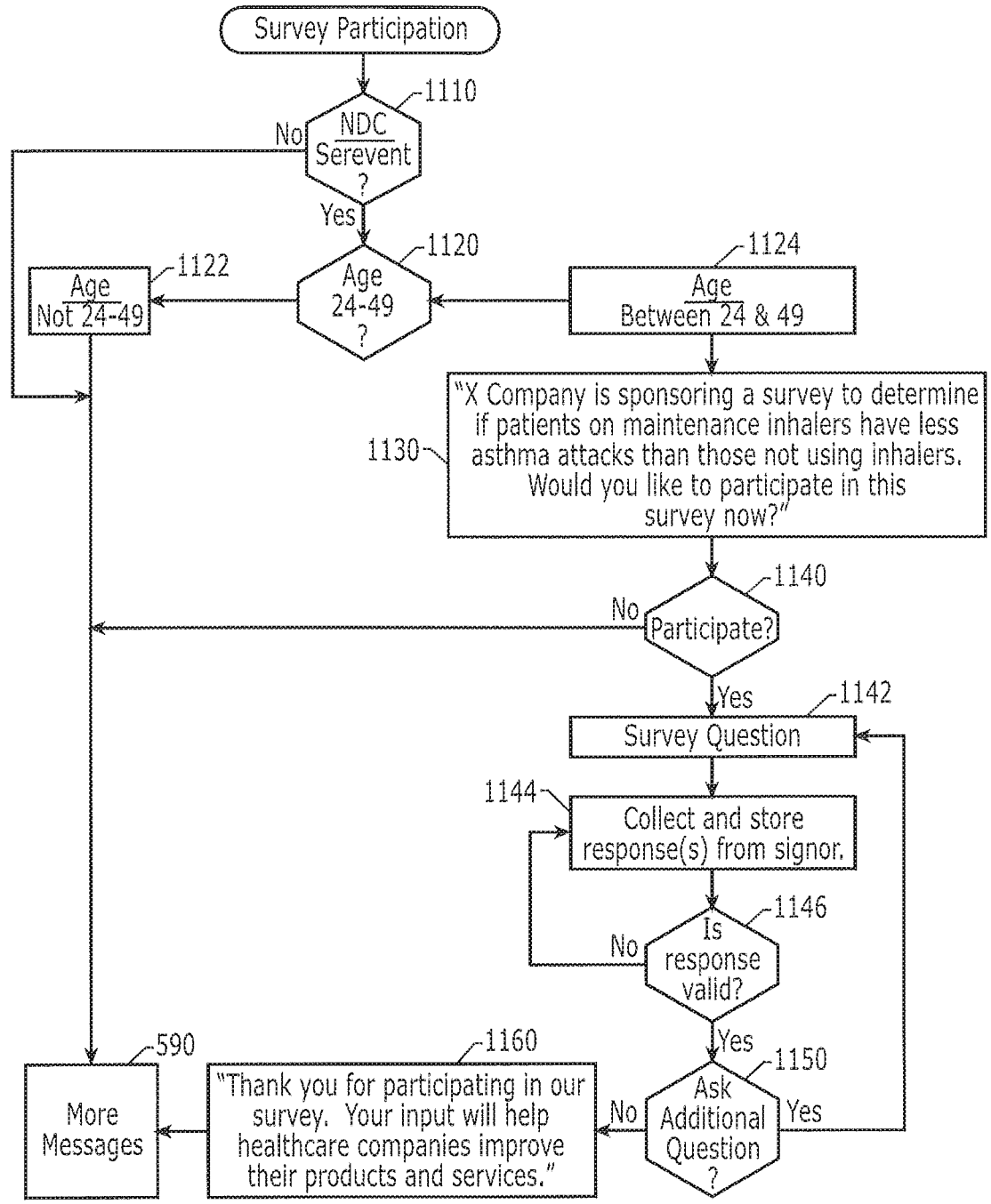

FIG. 11 is a flowchart of other embodiments of the present invention that may be used to provide a targeted message that solicits participation in a survey related to the pharmaceutical prescription and/or allows the patient to actually participate in the survey. It will be understood that, as used herein, a survey can be a clinical trial, a brief survey and/or other study that may be used in the pharmaceutical industry.

Referring now to FIG. 11, at Block 1110, a test is made as to whether the medication is identified as Serevent. At Block 1120, a test is made as to whether the age is between 24 and 49. If the tests at Blocks 1110 or 1120 fail, the prescription call flow may continue at Block 590. On the other hand, if at Block 1124 the age is between 24 and 49, then a targeted message may be displayed, at Block 1130, that indicates that a company is sponsoring a survey and asking if the patient would like to participate in a survey. At Block 1140, if the participant indicates that the patient wishes to participate, then at Block 1142, a survey question is asked. It will be understood by those having skill in the art that the question at Block 1140 may be asked to satisfy compliance rules for participation in the survey.

Continuing with the description of FIG. 11, at Block 1144, one or more responses are collected from the patient and tested for validity, at Block 1146. The response(s) may be stored. At Block 1150, if there are additional questions to ask, then the operations of Blocks 1142, 1144 and 1146 are repeatedly performed until there are no additional questions to ask. Once there are no additional questions to ask at Block 1150, a message may be displayed at Block 1160 that thanks the patient for participating in the survey. Accordingly, operations of FIG. 11 may be used to determine whether the age and/or gender qualifies the patient to participate in a study related to the pharmaceutical prescription and to identify a target message that solicits participation of the patient in the study related to the pharmaceutical prescription if the age and/or gender of the patient qualifies the patient to participate. Additional operations may be performed to display messages to the patient, to complete the study related to the pharmaceutical prescription. It also will be understood that other predetermined criteria may be used to solicit study participation in other embodiments.

Another embodiment of FIG. 11 now will be described. In these embodiments, rather than soliciting participation in a survey, participation in a clinical research study is solicited. Thus, in these embodiments, at Block 1110, the NDC is metformin hydrochloride, and at Block 1130, the display may read "There is a clinical research opportunity being conducted in your area for Type 2 diabetes. If you have had trouble controlling your blood glucose levels and are interested in learning more about the study opportunity, press 'Accept', otherwise press 'Decline'." In some embodiments, prior to, concurrent with and/or after providing the display of Block 1130, a display about the study sponsor's privacy policy, which may be different from general HIPPA requirements, may be provided. At Block 1142, additional questions may be asked, to further prequalify a patient candidate. For example, at Block 1142, a question may be displayed "Are you currently taking Celebrex?", and a response may be collected from the patient at Block 1144. Additional questions may be displayed at Block 1150 if desirable. For example, at Block 1150, an additional question can be displayed: "If you are interested in receiving a phone call about the clinical study, press 'Accept', otherwise 'Decline'." Finally, at Block 1160, a message can be displayed stating "Thank you for your interest in this study. You will be called." Accordingly, embodiments of FIG. 11 may also be used to solicit study participation.

Additional discussion of various embodiments of the present invention now will be provided. Some embodiments of the invention provide systems, methods and/or computer program products wherein, based on defined criteria including the treated patient's prescription medication(s) and associated applied business rules, the patient/caregiver candidate (defined as such, until either an opt-in or enrolled status is obtained) is presented in real time, targeted information via the electronic signature capture device at the pharmacy point of care. Embodiments of the present invention can be independently implemented in various different device technologies.

The logic and applied business rules can determine which patient candidates receive what presentment message. The business rules can include patient and/or medication attributes. In other embodiments, the business rules can include location (such as zip code), prescribing physician and payor information. The presentment message may contain static (branded/nonbranded) information, disease education, clinical research opportunities, dynamic information based on survey results, compliance and persistency programs, enrollment for medication refills, raise awareness, and many other displayed messages.

In some embodiments, the presentment message may represent ethnic diversity by language support. In other embodiments, the presentment message can be age and time of day appropriate. The messages may be reviewed for regulatory and legal efficacy by the appropriate governing body.

In some embodiments, Protected Health Information (PHI) or Personal Information (PI) need not be compromised. There can be effective controls regarding HIPPA and related security rules for both access control and entity authentication.

The signor may be provided with the information to determine if the signor is interested in receiving the information (opt-in) or the signor may decline the message. The patient candidate can acknowledge an interest by using the electronic signature capture device. The prompts may be displayed on the screen footprint with the designer's perspective for readability.

In some embodiments, the patient candidate's responses are captured and encrypted and stored in a deidentified format. Opt-in responses may be excluded per the project protocol on a per business case basis. The electronic signature capture device may also operate on a time out basis in some embodiments, so that after the elapsed time has passed all information including the presentment activity can be replaced with a generic pharmacy message on the device display. The electronic signature capture device may be a stand alone unit or an integrated multipurpose unit. In some embodiments, the normal flow of the pharmacy transaction may be resumed without disruption at the point of opt-in acknowledgement or a message to client response. The treated patient's signature may be obtained on the electronic signature device for pharmacy prescription pick up, HIPPA acknowledgment, opt-in acknowledgment demonstrative of interest and participation and/or for any other purposes.

Figure 12:
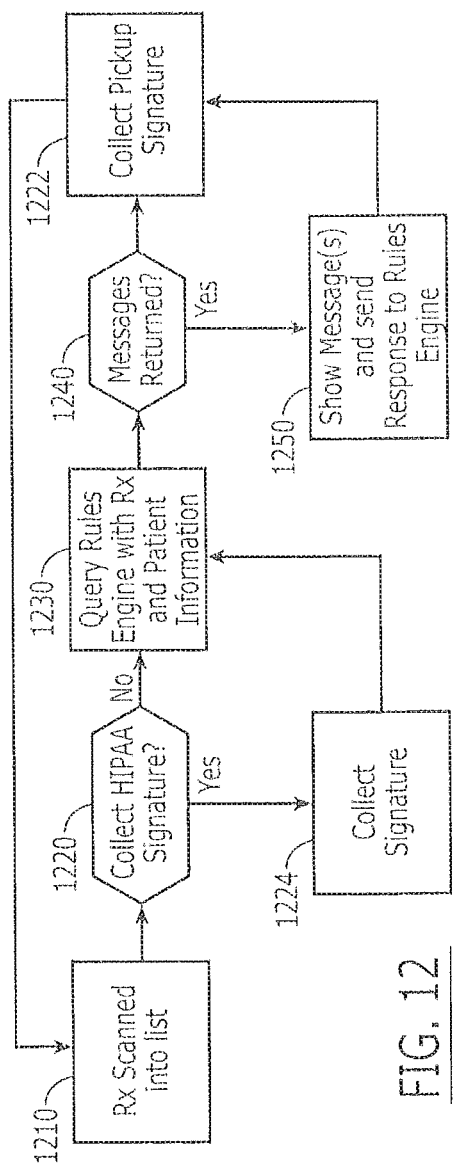
FIG. 12 is a flowchart of operations that may be performed to provide targeted messages according to yet other embodiments of the present invention.

FIG. 12 is a flowchart of operations that may be performed to display targeted messages in connection with HIPPA signature collection and prescription pick up, according to some embodiments of the present invention. Referring to FIG. 12, as shown at Block 1210, a prescription identification is scanned into a list, which may correspond to the operations at Block 210 as described above. At Block 1220 it may be desirable to collect a HIPPA signature and if so, at Block 1224 the HIPPA signature is accepted, which may correspond to Block 220 described above. At Block 1230 the rules engine is queried, which may correspond to Block 230 described above. If a message is identified at Block 1240, which may correspond to Block 240 described above, then messages are displayed at Block 1250, which may correspond to Block 250 described above. A pick up signature 1222 may then be obtained at Block 1222. Accordingly, in embodiments of FIG. 12, messages may be displayed after a HIPPA signature is collected at Block 1220 but before a pick up signature is collected at Block 1222. Additional generic messages may be displayed during a screen saver. In querying a rules engine with the prescription and patient information at Block 1230, the treated patient caregiver may be identified by a single attribute or combination of attributes as shown in FIGS. 13A, 13B and/or 13C. The field names are representative of information that may be present at the time of transaction but shall not be construed as limiting. The field names of FIGS. 13A-13C may correspond to the databases in the pharmacy dispensing system 535 of FIG. 5A. As discussed earlier, in some embodiments, personal identifying data from the fields in the pharmacy dispensing system database(s), such as name, social security number etc., may be removed when the predefined criteria (based on the identification of the prescription) is retrieved.

EXAMPLE

The following example shall be regarded as merely illustrative and shall not be construed as limiting the invention. This example will illustrate enrolling sample patients into a marketing programs using two messaging opportunities to improve participation, and may correspond to the operations that were generally described in FIG. 11. The process flow in the pharmacy at the point of customer prescription pickup may be as follows:

Step 1 Customer goes to the normal prescription pick up counter to pick up a requested prescription.

Step 2 Pharmacy retrieves the prescription per normal practices.

Step 3 The prescription number is scanned or manually entered at the signature capture station.

Step 4 The prescription information is displayed. See FIG. 14A (in some embodiments, personal identifying data may not appear).

Step 5 If one or more of the customers' acknowledgments has not been obtained, then the following will occur:
A screen is displayed to capture the customer's signature for acknowledgment.
The pharmacy associate shows the customer the pharmacy's privacy policy.
The customer or representative of the customer signs to acknowledge that they have been provided the privacy policy.
The date, time, acknowledgment version, and signature are saved electronically.

Step 6 Based on the business rules; (e.g., patient is 18 yrs or older, prior presentment), the marketing campaign messaging is displayed for customer opt-in. Message presentment may be a maximum of 2× per patient.

Step 7 The customer is presented with the option to participate in the program with the following message text displayed on the screen of FIG. 14B:

Would you be interested in enrolling in a FREE patient education program that entitles you to acid reflux disease news, tips on nutrition and lifestyle choices to help manage heartburn, and discounts on your prescription? If you enroll, you will receive ongoing mailings with information about acid reflux disease, in addition to money-saving offers on your prescription.

Would you like us to automatically enroll you into the program? Press Accept (#) to enroll now, otherwise (#) to Decline. To read our full Privacy Policy regarding the use of information we collect during this program, press Privacy Statement.

Step 8 If the customer pressed Privacy Statement, the customer is presented with the Privacy Policy Notice of FIG. 14C.

Step 9 The customer signs the third party disclaimer for all of the prescriptions using the screen of FIG. 14D.

Step 10 The information for each prescription along with the customer's signature is saved.

Step 11 The pharmacy associate completes the transaction; e.g., rings the prescription up at the point of sale, receives payment, and hands the customer their prescription. If patient chooses to opt in the marketing campaign, the patient address information is automatically collected from the pharmacy system and provided to marketing who will fulfill this request via U.S. Mail.

Embodiments of the invention have described the display of targeted messages on a signature capture system. In other embodiments, targeted messages also may be provided as part of the interactive voice response system 120 as described in application Ser. No. 10/672,556 to DiVenuta et al. entitled Methods, Systems and Computer Program Products for Providing Targeted Messages for Pharmacy Interactive Voice Response (IVR) Systems, filed Sep. 25, 2003 assigned to the assignee of the present application, the disclosure of which is hereby incorporated in its entirety as if set forth fully herein.

Figure 15:
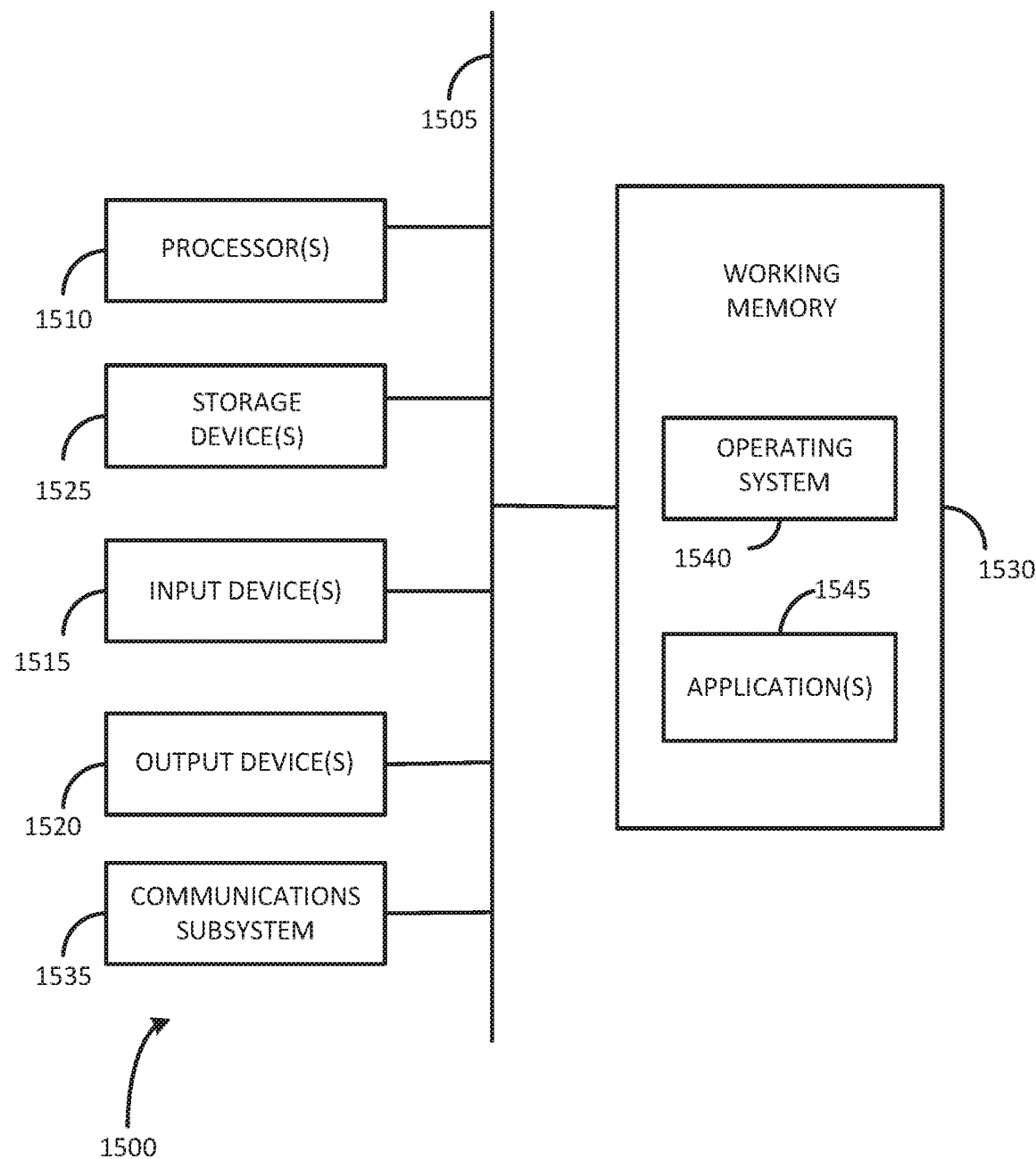
FIG. 15 is a block diagram illustrating a specialized computer system upon which embodiments of the present invention may be implemented.

FIG. 15 is a block diagram illustrating a specialized computer system upon which embodiments of the present invention may be implemented. This example illustrates a computer system 1500 such as may be used, in whole, in part, or with various modifications, and with software, as specially programmed systems that provide the overall functions of the pharmacy management system 100, or the functions of the pharmacy dispensing system 130 and targeted message module 140, as well as other components and functions of the invention described herein.

The computer system 1500 is shown comprising hardware elements that can be electrically coupled or otherwise in communication via a bus 1505. The hardware elements can include one or more processors 1510 (such as digital signal processing chips, graphics acceleration chips, and/or the like); one or more input devices 1515, which can include, without limitation, a mouse, a keyboard and/or the like; and one or more output devices 1520, which can include, without limitation, a display device, a printer and/or the like.

The computer system 1500 may further include one or more storage devices 1525, which can comprise, without limitation, local and/or network accessible storage or memory systems having computer or machine readable media. Common forms of physical and/or tangible computer readable media include, as examples, a floppy disk, a flexible disk, hard disk, magnetic tape, or any other magnetic medium, an optical medium (such as CD-ROM), a random access memory (RAM), a read only memory (ROM) which can be programmable or flash-updateable or the like, and any other memory chip, cartridge, or medium from which a computer can read data, instructions and/or code. In many embodiments, the computer system 1500 will further comprise a working memory 1530, which could include (but is not limited to) a RAM or ROM device, as described above. The computer system 1500 also may further include a communications subsystem 1535, such as (without limitation) a modem, a network card (wireless or wired), an infra-red communication device, or a wireless communication device and/or chipset, such as a Bluetooth® device, an 802.11 device, a WiFi device, a WiMax device, a near field communications (NFC) device, cellular communication facilities, etc. The communications subsystem 1535 may permit data to be exchanged with a network, and/or any other devices described herein. Transmission media used by communications subsystem 1535 (and the bus 1505) may include copper wire, coaxial cables and fiber optics. Hence, transmission media can also take the form of waves (including, without limitation radio, acoustic and/or light waves, such as those generated during radio-wave and infra-red data communications).

The computer system 1500 can also comprise software elements, illustrated within the working memory 1530, including an operating system 1540 and/or other code, such as one or more application programs 1545, which may be designed to provide the unique computer functions implemented in the processes seen in FIGS. 2, 3, 5A, 5B, and 6-12, and thus provide a specially designed and programmed device (e.g., pharmacy management system 100, including the signature capture device 170) for carrying out the unique elements and novel features described herein.

As an example, one or more methods discussed earlier might be implemented as code and/or instructions executable by a computer (and/or a processor within a computer). In some cases, a set of these instructions and/or code might be stored on a computer readable storage medium that is part of the system 1500, such as the storage device(s) 1525. In other embodiments, the storage medium might be separate from a computer system (e.g., a removable medium, such as a compact disc, etc.), and/or provided in an installation package with the instructions/code stored thereon. These instructions might take the form of code which is executable by the computer system 1500 and/or might take the form of source and/or installable code, which is compiled and/or installed on the computer system 1500 (e.g., using any of a variety of generally available compilers, installation programs, compression/decompression utilities, etc.). The communications subsystem 1535 (and/or components thereof) generally will receive the signals (and/or the data, instructions, etc., carried by the signals), and the bus 1505 then might carry those signals to the working memory 1530, from which the processor(s) 1505 retrieves and executes the instructions. The instructions received by the working memory 1530 may optionally be stored on storage device 1525 either before or after execution by the processor(s) 1510.

While various functionalities are ascribed to certain individual system components, unless the context dictates otherwise, this functionality can be distributed or combined among various other system components in accordance with different embodiments of the invention. As one example, the systems seen in FIGS. 1 and 4A-4B may be each implemented by a single system having one or more storage device and processing elements, or may each be implemented by plural systems, with their respective functions distributed across different systems either in one location or across a plurality of linked locations.

Moreover, while the various flows and processes described herein (e.g., those illustrated in FIGS. 2, 3, 5A, 5B, and 6-12) are described in a particular order for ease of description, unless the context dictates otherwise, various procedures may be reordered, added, and/or omitted in accordance with various embodiments of the invention. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments may be described with (or without) certain features for ease of description and to illustrate exemplary features, the various components and/or features described herein with respect to a particular embodiment can be substituted, added, and/or subtracted to provide other embodiments, unless the context dictates otherwise. Consequently, although the invention has been described with respect to exemplary embodiments, it will be appreciated that the invention is intended to cover all modifications and equivalents within the scope of the following claims.

What is claimed is:

1. A method for managing the security of personal information at a pharmacy management system that processes ordered items using a signature capture device, the method comprising:

receiving identification of an ordered item at the pharmacy management system, the ordered item being a pharmaceutical prescription to be filled with a supply of the ordered item;

accepting, at the signature capture device in the pharmacy management system, a signature from a person receiving the ordered item;

querying a first database in the pharmacy management system, using the identification of the ordered item, to retrieve predefined criteria based on the identification of the ordered item, wherein the retrieved predefined criteria does not include personal identifying data for the person receiving the ordered item, the first database comprising a pharmacy dispensing database and the predefined criteria comprising patient data and prescription data stored in the pharmacy dispensing database, with the prescription data including a last fill date for the ordered item and a day's supply for the ordered item on the last fill date;

querying a second database in the pharmacy management system using the predefined criteria to identify a targeted message, wherein, with the predefined criteria to identify the targeted message not including personal identifying data for the person receiving the ordered item, the targeted message does not provide information to identify the person receiving the ordered item, and wherein the targeted message is based on the last fill date for the ordered item and the day's supply for the ordered item on the last fill date;

displaying the targeted message on the signature capture device for viewing by the person receiving the ordered item, wherein the targeted message is removed from the signature capture device after a predetermined period of time, the predetermined period of time chosen to avoid a subsequent person at the signature capture device viewing the targeted message;

receiving, at the signature capture device, a response to the targeted message from the person receiving the ordered item; and providing the received response to a third database in the pharmacy management system, including de-identifying the received response to maintain the privacy of personal information of the person receiving the ordered item.

2. The method of claim 1, wherein the targeted message includes one of:
(1) a reminder on use of the ordered item; and
(2) an indication of an alternative medication for the ordered item.

3. The method of claim 2, wherein receiving identification of the ordered item comprises at least one of:
receiving a bar code scan of a bar code on a container that corresponds to the pharmaceutical prescription;
receiving input of a pharmaceutical prescription number that corresponds to the pharmaceutical prescription; and
receiving input of identification information that can be used to identify the pharmaceutical prescription.

4. The method of claim 2, wherein accepting a signature comprises accepting a signature on the signature capture device to acknowledge at least one of:
pharmaceutical prescription receipt;
Health Insurance Portability & Accountability Act (HIPAA) information receipt;
credit card/debit card payment; and
a desire to receive the targeted message.

5. The method of claim 1, further comprising:
validating the received identification of an ordered item, by verifying the format of the identification.

6. The method of claim 1, further comprising validating the response to the targeted message, by verifying the format of the response.

7. The method of claim 1, wherein the signature capture device includes a signature capture touch screen and wherein displaying the targeted message is performed on the signature capture touch screen.

8. The method of claim 1, wherein the second database is a messaging rules database, including a rules engine to determine if the targeted message corresponds to the predefined criteria.

9. The method of claim 1, wherein the third database is a logging database for logging messages and responses at the signature capture device.

10. The method of claim 1, wherein displaying the targeted message on the signature capture device is in response to accepting the signature from the person at the signature capture device.

11. The method of claim 1, wherein the predefined criteria used to identify the targeted message includes both prescription data and non-personal identifying data in the patient data, taken from a group comprising patient age, patient gender, medication type and prescription history.

12. A pharmacy management system, comprising:
a pharmacy dispensing database storing predefined criteria, comprising patient data and prescription data, relating to each of a plurality of prescriptions;
a messaging rules database that identifies each of a plurality of targeted messages;
a logging database for storing information relating to the targeted messages; and
a signature capture device for receiving a signature and displaying the targeted messages;
wherein the pharmacy management system includes a processor and a memory, wherein the memory stores instructions which, when executed by the processor, cause the pharmacy management system to:

receive identification of a specific prescription to be filled with a supply of a prescribed item;
accept a signature from a customer at the signature capture device;
query the pharmacy dispensing database, using the identification of the specific prescription, to retrieve predefined criteria based on the identification of the specific prescription, wherein the retrieved predefined criteria does not include personal identifying data for the customer, with the prescription data in the retrieved predefined criteria including a last fill date for the prescribed item and a day's supply for the prescribed item on the last fill date;
query the messaging rules database, using the retrieved predefined criteria based on the identification of the specific prescription, to identify a targeted message, wherein, with the predefined criteria to identify the targeted message not including personal identifying data for the customer receiving the prescribed item, the targeted message does not provide information to identify the customer receiving the prescribed item, and wherein the targeted message is based on the last fill date for the prescribed item and the day's supply for the prescribed item on the last fill date;
display the targeted message on the signature capture device for viewing by the customer, wherein the targeted message is removed from the signature capture device after a predetermined period of time, the predetermined period of time chosen to avoid a subsequent person at the signature capture device viewing the targeted message;
receive a response to the targeted message from the customer at the signature capture device; and
provide the received response to the logging database, including de-identifying the received response to maintain the privacy of personal information of the customer.

13. The system of claim 12, wherein the instructions executed by the processor that cause the pharmacy management system to:
validate the received identification of the specific prescription, by verifying the format of the identification.

14. The system of claim 12, wherein the instructions executed by the processor further cause the pharmacy management system to:
validate the response to the targeted message, by verifying the format of the response.

15. The system of claim 12, wherein causing the pharmacy system to receive identification of a specific prescription comprises at least one of:
receiving a bar code scan of a bar code on a container that corresponds to the specific prescription;
receiving input of a pharmaceutical prescription number that corresponds to the specific prescription; and
receiving input of identification information that can be used to identify the specific prescription.

16. The system of claim 12, wherein causing the pharmacy system to accept a signature from the customer at the signature capture device comprises accepting a signature on the signature capture device to acknowledge at least one of:
pharmaceutical prescription receipt;
Health Insurance Portability & Accountability Act (HIPAA) information receipt;
credit card/debit card payment; and
a desire to receive the targeted message.

17. The system of claim 12, wherein the signature capture device includes a signature capture touch screen and wherein the display of the targeted message is performed on the signature capture touch screen.

18. The system of claim 12, wherein the predefined criteria used to identify the targeted message includes both prescription data and non-personal identifying data in the patient data, taken from a group comprising patient age, patient gender, medication type and prescription history.

* * * * *

UNITED STATES PATENT AND TRADEMARK OFFICE
CERTIFICATE OF CORRECTION

PATENT NO. : 10,643,003 B2
APPLICATION NO. : 16/215034
DATED : May 5, 2020
INVENTOR(S) : Godwin et al.

It is certified that error appears in the above-identified patent and that said Letters Patent is hereby corrected as shown below:

On the Title Page

Item (63), Column 1 Line 6 under Related U.S. Application Data:
Delete "which is a continuation-in-part of application No. 13/102,570, filed on May 6, 2011, now abandoned, which is a continuation-in-part of application No. 11/375,516, filed on Mar. 14, 2006, now abandoned." and insert -- U.S. application No. 13/102,570, filed on May 6, 2011, now abandoned is also a Continuation-in-Part of U.S. application No. 11/375,516, filed on Mar. 14, 2006, now abandoned. --, therefor.

In the Drawings

Sheet 10 of 22, Reference Numeral 860, Fig 8, Line 5:
Delete "ashma." and insert -- asthma. --, therefor.

In the Specification

Column 7 Line 53:
Delete "HIPPA" and insert -- HIPAA --, therefor.

Column 11 Line 48:
Delete "Lantis" and insert -- Lantus --, therefor.

Column 14 Line 45:
Delete "Fosomax" and insert -- Fosamax --, therefor.

Column 15 Line 58:
Delete "HIPPA" and insert -- HIPAA --, therefor.

Column 16 Line 36:
Delete "HIPPA" and insert -- HIPAA --, therefor.

Signed and Sealed this
Sixth Day of October, 2020

Andrei Iancu
*Director of the United States Patent and Trademark Office*

CERTIFICATE OF CORRECTION (continued)
U.S. Pat. No. 10,643,003 B2

Column 16 Line 60:
Delete "HIPPA" and insert -- HIPAA --, therefor.

Column 16 Line 65:
Delete "HIPPA" and insert -- HIPAA --, therefor.

Column 17 Line 3:
Delete "HIPPA" and insert -- HIPAA --, therefor.

Column 17 Line 4:
Delete "HIPPA" and insert -- HIPAA --, therefor.

Column 17 Line 13:
Delete "HIPPA" and insert -- HIPAA --, therefor.